(12) United States Patent
Ghiaur et al.

(10) Patent No.: US 11,648,222 B2
(45) Date of Patent: May 16, 2023

(54) USE OF CYP26-RESISTANT RAR ALPHA SELECTIVE AGONISTS IN THE TREATMENT OF CANCER

(71) Applicants: Io Therapeutics, Inc., Houston, TX (US); The Johns Hopkins University, Baltimore, MD (US)

(72) Inventors: Gabriel Ghiaur, Baltimore, MD (US); Richard J. Jones, Baltimore, MD (US); Salvador Alonso, Baltimore, MD (US); Roshantha A. Chandraratna, San Juan Capistrano, CA (US)

(73) Assignees: IO Therapeutics, Inc., Spring, TX (US); The Johns Hopkins Univercity, Baltimore, MD (US)

(*) Notice: Subject to any disclaimer, the term of this patent is extended or adjusted under 35 U.S.C. 154(b) by 0 days.

(21) Appl. No.: 17/136,428

(22) Filed: Dec. 29, 2020

(65) Prior Publication Data
US 2021/0137866 A1 May 13, 2021

Related U.S. Application Data

(62) Division of application No. 15/777,868, filed as application No. PCT/US2016/063659 on Nov. 23, 2016, now Pat. No. 10,940,127.

(60) Provisional application No. 62/260,098, filed on Nov. 25, 2015.

(51) Int. Cl.
| | | |
|---|---|---|
| A61K 31/196 | (2006.01) | |
| A61K 45/06 | (2006.01) | |
| A61K 31/192 | (2006.01) | |
| A61K 31/4166 | (2006.01) | |
| A61K 31/454 | (2006.01) | |
| A61K 31/4196 | (2006.01) | |
| A61K 31/138 | (2006.01) | |
| A61K 31/58 | (2006.01) | |
| A61K 31/4545 | (2006.01) | |
| A61K 31/5685 | (2006.01) | |
| A61K 31/277 | (2006.01) | |
| A61P 35/00 | (2006.01) | |
| A61K 31/69 | (2006.01) | |

(52) U.S. Cl.
CPC .......... *A61K 31/196* (2013.01); *A61K 31/138* (2013.01); *A61K 31/192* (2013.01); *A61K 31/277* (2013.01); *A61K 31/4166* (2013.01); *A61K 31/4196* (2013.01); *A61K 31/454* (2013.01); *A61K 31/4545* (2013.01); *A61K 31/5685* (2013.01); *A61K 31/58* (2013.01); *A61K 31/69* (2013.01); *A61K 45/06* (2013.01); *A61P 35/00* (2018.01)

(58) Field of Classification Search
CPC ...... A61K 31/196; A61K 31/138; A61P 35/00
See application file for complete search history.

(56) References Cited

U.S. PATENT DOCUMENTS

| | | | |
|---|---|---|---|
| 4,326,055 A | 4/1982 | Loeliger | |
| 4,362,892 A | 12/1982 | Hindley et al. | |
| 5,234,926 A | 8/1993 | Chandraratna | |
| 5,324,840 A | 6/1994 | Chandraratna | |
| 5,612,356 A | 3/1997 | Yoshimura et al. | |
| 5,723,666 A | 3/1998 | Vuligonda et al. | |
| 5,739,338 A | 4/1998 | Beard et al. | |
| 5,776,699 A | 7/1998 | Klein et al. | |
| 5,824,685 A | 10/1998 | Campochiaro et al. | |
| 5,877,207 A | 3/1999 | Klein et al. | |
| 5,919,970 A | 7/1999 | Song et al. | |
| 5,958,954 A | 9/1999 | Klein et al. | |
| 5,965,606 A * | 10/1999 | Teng | A61K 31/44 514/456 |
| 6,037,488 A | 3/2000 | Song et al. | |
| 6,225,494 B1 | 5/2001 | Song et al. | |
| 6,387,950 B2 | 5/2002 | Nehme et al. | |
| 6,452,032 B1 | 9/2002 | Beard et al. | |
| 6,455,701 B1 | 9/2002 | Song et al. | |
| 6,534,544 B1 | 3/2003 | Teng et al. | |
| 6,653,322 B1 | 11/2003 | Chambon et al. | |
| 6,942,980 B1 | 9/2005 | Klein | |
| 7,468,391 B2 | 12/2008 | Vasudevan et al. | |
| 7,476,673 B2 | 1/2009 | Tsang et al. | |
| 8,252,837 B2 | 8/2012 | Ekimoto | |
| 8,673,321 B2 | 3/2014 | Brodsky et al. | |
| 9,868,994 B2 * | 1/2018 | McKeown | A61K 45/06 |
| 9,907,768 B2 | 3/2018 | Chandraratna et al. | |
| 10,004,708 B2 | 6/2018 | Chandraratna et al. | |

(Continued)

FOREIGN PATENT DOCUMENTS

| | | |
|---|---|---|
| CA | 2974066 | 6/2016 |
| EP | 0661259 | 7/1995 |

(Continued)

OTHER PUBLICATIONS

Knapper (Expert Opinion on Investigational Drugs (2011) 20:1377-1395) (Year: 2011).*

(Continued)

*Primary Examiner* — Marcos L Sznaidman

(74) *Attorney, Agent, or Firm* — K&L Gates LLP; Louis C. Cullman; Michelle Glasky Bergman

(57) ABSTRACT

Disclosed herein are methods for treating a cancer comprising administering to a subject in need thereof an effective dose of a CYP26-resistant retinoic acid receptor (RAR) alpha (RARα) selective agonist, whereby as a result of the treatment the tumor burden is reduced in the subject and cancer stem cells resident in the bone marrow are substantially reduced.

11 Claims, 12 Drawing Sheets

(56) References Cited

U.S. PATENT DOCUMENTS

| | | | |
|---|---|---|---|
| 10,004,709 | B2 | 6/2018 | Chandraratna et al. |
| 10,213,401 | B2 | 2/2019 | Chandraratna et al. |
| 10,940,127 | B2 | 3/2021 | Ghiaur et al. |
| 2001/0018456 | A1 | 8/2001 | Fesus et al. |
| 2005/0148590 | A1 | 7/2005 | Tsang |
| 2007/0077652 | A1 | 4/2007 | Peled et al. |
| 2008/0300312 | A1 | 12/2008 | Chandraratna |
| 2009/0105200 | A1 | 4/2009 | Keegan et al. |
| 2009/0176862 | A1 | 7/2009 | Chandraratna et al. |
| 2009/0181988 | A1 | 7/2009 | Welsh |
| 2009/0203720 | A1 | 8/2009 | Zhao |
| 2011/0159111 | A1 | 6/2011 | Curry et al. |
| 2011/0237802 | A1 | 9/2011 | Rangineni et al. |
| 2011/0319427 | A1* | 12/2011 | Schimmer .............. A61K 45/06 514/255.06 |
| 2013/0150408 | A1 | 6/2013 | Liu et al. |
| 2014/0086909 | A1 | 3/2014 | Lu |
| 2015/0290194 | A1 | 10/2015 | Wang et al. |
| 2015/0322155 | A1* | 11/2015 | Zhao ..................... C07D 498/14 546/187 |
| 2016/0317654 | A1 | 11/2016 | Noelle |
| 2017/0354623 | A1 | 12/2017 | Chandraratna et al. |
| 2018/0133179 | A1 | 5/2018 | Chandrartna et al. |
| 2018/0133180 | A1 | 5/2018 | Chandrartna et al. |
| 2018/0133181 | A1 | 5/2018 | Chandrartna et al. |
| 2018/0133182 | A1 | 5/2018 | Chandrartna et al. |
| 2018/0133183 | A1 | 5/2018 | Chandrartna et al. |
| 2021/0137865 | A1 | 5/2021 | Ghiaur et al. |
| 2022/0184013 | A1 | 6/2022 | Ghiaur et al. |

FOREIGN PATENT DOCUMENTS

| | | | |
|---|---|---|---|
| WO | 2001/007028 | A2 | 2/2001 |
| WO | 2002/028810 | A2 | 4/2002 |
| WO | 2007/041398 | A2 | 4/2007 |
| WO | 2008/091620 | A2 | 7/2008 |
| WO | 2008121570 | | 10/2008 |
| WO | WO 2009/147169 | * | 12/2009 |
| WO | 2015/092420 | A1 | 6/2015 |
| WO | 2016144976 | A1 | 9/2016 |
| WO | 2017091762 | | 6/2017 |
| WO | 2017/214575 | A1 | 12/2017 |

OTHER PUBLICATIONS

Beard et. al. (Bioorg. Med. Chem. Lett (2002) 12:3145-3148). (Year: 2002).*

Chee et. al. (Leukemia (2013) 27:1369-1380). (Year: 2013).*

* cited by examiner

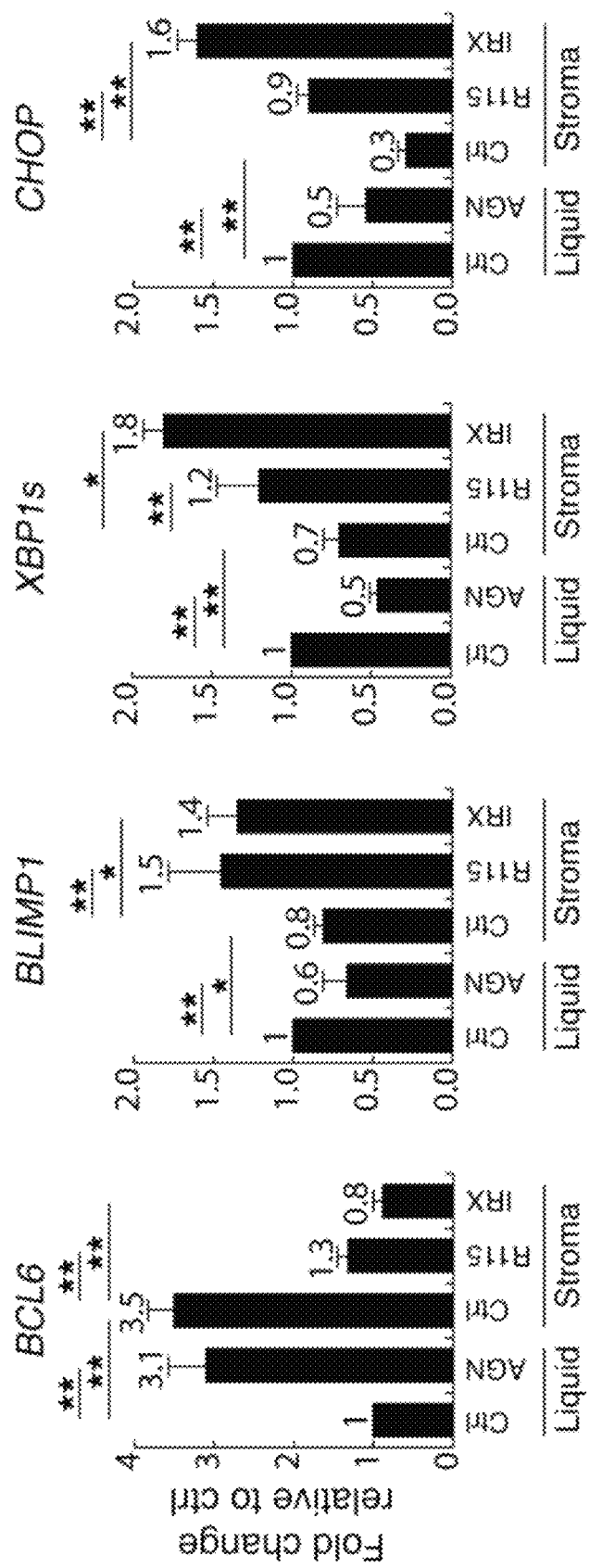

USE OF CYP26-RESISTANT RAR ALPHA SELECTIVE AGONISTS IN THE TREATMENT OF CANCER

CROSS-REFERENCE TO RELATED APPLICATIONS

This application is a divisional of U.S. patent application Ser. No. 15/777,868, filed May 21, 2018, now U.S. Pat. No. 10,940,127, which is a 35 U.S.C. 371 national phase entry of PCT/US2016/063659, filed Nov. 23, 2016, which claims the benefit of U.S. provisional patent application 62/260,098 filed Nov. 25, 2015; the entire contents of which are each incorporated by reference herein.

STATEMENT REGARDING FEDERALLY-SPONSORED RESEARCH

This invention was made with government support under HL127269 and CA015396 awarded by the National Institutes of Health. The government has certain rights in the invention.

FIELD

Disclosed herein are methods of treating cancer with CYP26-resistant retinoic acid receptor alpha (RARα) selective agonists.

BACKGROUND

Normal hematopoietic stem cells (HSCs) are primed to be highly sensitive to retinoids but are maintained in a retinoid signaling-naïve state by isolating them from physiologic levels of retinoids. The bone marrow microenvironment, by expression of the enzyme CYP26 metabolically inactivates retinoic acid, regulates the exposure of the bone marrow to retinoids. This mechanism (CPY26-mediated retinoid metabolism) is dynamic and used by the bone marrow stroma to match HSC behavior to physiological needs. For example, steady state low levels of retinoids in the bone marrow niche maintains HSCs in a quiescent state, while during situations of stress (i.e., exposure to radiation or chemotherapy) higher retinoid levels are maintained to recruit HSCs into cell division and rescue hematopoiesis.

In subjects with hematologic malignancies, cancer HSCs are protected from retinoids by stromal CYP26, in a similar fashion to the normal situation. However, because of other alterations in the bone marrow niche in hematologic malignancies, such as differences in aldehyde dehydrogenase (ALDH) activity, there exists a therapeutic window for retinoids to be useful in the treatment of hematologic malignancies. Expression of CYP26 by the bone marrow microenvironment contributes to the protection of immature acute myeloid leukemia (AML) cells from all-trans retinoic acid (ATRA) and may explain why ATRA is not effective in treating AML. Exposure to pharmacological concentrations of ATRA acting through retinoic acid receptor gamma (RARɎ), induces CYP26 expression in the bone marrow microenvironment, thus protecting the cancer stem cells therein from retinoid activity. However, the use of retinoid analogs which are not inactivated by CYP26 enables such retinoids to terminally differentiate and thus eliminate the cancer HSCs from the protective bone marrow niche. Since such differentiation is mediated by RARα, and the use of RARα specific analogs, which are CYP26 resistant, enables the therapeutic differentiation-inducing activity without inactivation by the CYP26 enzyme.

SUMMARY

Disclosed herein are methods of treating cancer with CYP26-resistant, retinoic acid receptor (RAR) alpha (RARα) selective agonists and their use in the treatment of malignancies by acting upon cancer stem cells resident in the bone marrow.

Thus, provided herein are methods for treating a hematologic malignancy comprising administering to a subject in need thereof an effective dose of a CYP26-resistant RARα selective agonist, whereby as a result of the treatment the tumor burden is reduced in the subject.

In some embodiments, administration of an effective dose of the CYP26-resistant RARα selective agonist results in the elimination of minimal residual disease or cancer stem cells from the bone marrow niche of the subject, thereby rendering the subject substantially free of cancer. In certain embodiments, administration of an effective dose of the CYP26-resistant RARα selective agonist results in sensitization of minimal residual disease to other anticancer agents, whereby combination of the CYP26-resistant RARα selective agonist with other anticancer agents results in elimination of minimal residual disease or cancer stem cells from the bone marrow niche of the subject, thereby rendering the subject substantially free of cancer.

In certain embodiments, the cancer stem cell is a hematologic cancer stem cell (HSC). In some embodiments, the hematologic malignancy is acute myeloid leukemia (AML), chronic myelogenous leukemia (CML), accelerated CML, CML blast phase (CML-BP), acute lymphoblastic leukemia (ALL), chronic lymphocytic leukemia (CLL), Hodgkin's disease (HD), non-Hodgkin's lymphoma (NHL), follicular lymphoma, mantle cell lymphoma, B-cell lymphoma, T-cell lymphoma, multiple myeloma (MM), Waldenstrom's macroglobulinemia, a myelodysplastic syndrome (MDS), refractory anemia (RA), refractory anemia with ringed siderblasts (RARS), refractory anemia with excess blasts (RAEB), RAEB in transformation (RAEB-T), or a myeloproliferative syndrome.

In certain embodiments, the CYP26-resistant RARα selective agonist is

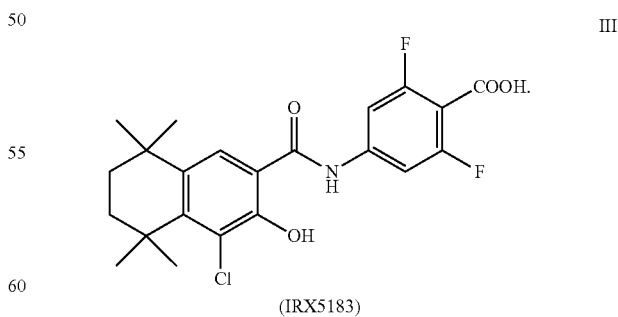

(IRX5183)

III

In other embodiments, the CYP26-resistant RARα selective agonist is tamibarotene (AM80), AM580, or Re 80.

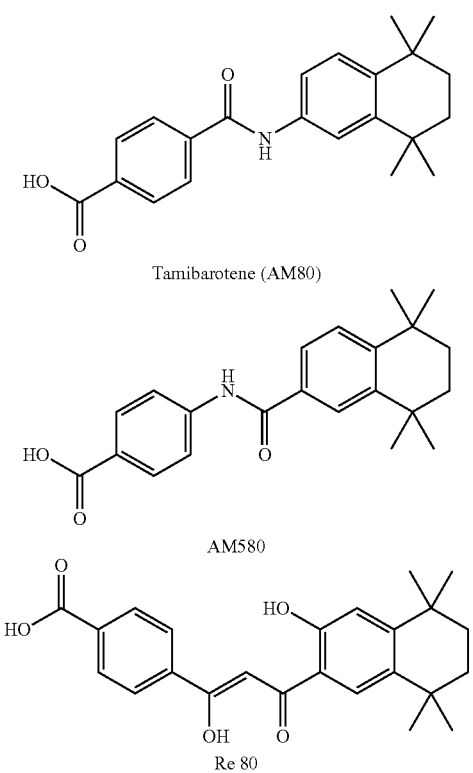

Tamibarotene (AM80)

AM580

Re 80

In some embodiments, as a result of the administration, the subject remains in remission longer than 5 years.

Also disclosed herein are methods for treating a solid tumor malignancy comprising administering to a subject in need thereof an effective dose of a CYP26-resistant RARα selective agonist, and at least one additional anti-cancer agent, whereby as a result of the treatment, the tumor burden is reduced in the subject.

In certain embodiments, administration of an effective dose of a RARα agonist which is not metabolized by CYP26 results in the elimination of minimal residual disease or cancer stem cells in the bone marrow niche of the subject, thereby rendering the subject substantially free of cancer.

In some embodiments, the solid tumor malignancy is a type of cancer which typically metastasizes to the bone marrow. In some embodiments, the additional anti-cancer agent is an agent listed in Table 1. In certain embodiments, the solid tumor malignancy is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, brain cancer, bone cancer, or soft tissue sarcoma.

In some embodiments, the additional anti-cancer agent is selected from the combinations in Table 1. In certain embodiments, the additional anti-cancer agent is trastuzumab, tamoxifen, anastrazole, exemestrane, letrozole, crizotinib, aberatrone, enzalutamide, bicalutemide, bortezomib, or thalidomide.

In some embodiments, as a result of the administration, the subject remains in remission longer than 1 year, longer than 2 years, longer than 3 years, longer than 4 years, or longer than 5 years.

In some embodiments, as a result of the administration, the subject remains in remission for at least 1 year (e.g., 1-2 years, 1-3 years, 1-4 years, 1-5 years, 2-3 years, 2-4 years, 2-5 years, 3-4 years, 3-5 years, or 4-5 years).

In some embodiments, as a result of the administration, the subject remains in remission for 1-2 years, 1-3 years, 1-4 years, or 1-5 years.

Also disclosed herein are methods for treating cancer, comprising administering to a subject in need thereof a CYP26-resistant retinoic acid receptor alpha (RARα) selective agonist and bortezomib.

Also disclosed herein are methods for treating cancer, comprising administering to a subject in need thereof an effective dose of a CYP26-resistant retinoic acid receptor alpha (RARα) selective agonist and bortezomib.

Also disclosed herein are methods for treating cancer, comprising administering to a subject in need thereof an effective dose of a CYP26-resistant retinoic acid receptor alpha (RARα) selective agonist and bortezomib, whereby as a result of the treatment the tumor burden is reduced in the subject.

Also disclosed herein are methods for treating multiple myeloma comprising administering to a subject in need thereof an effective dose of a CYP26-resistant retinoic acid receptor alpha (RARα) selective agonist and bortezomib, whereby as a result of the treatment the tumor burden is reduced in the subject.

Also disclosed herein are methods for treating multiple myeloma comprising administering to a subject in need thereof an effective dose of a IRX5183 and bortezomib, whereby as a result of the treatment the tumor burden is reduced in the subject.

Also disclosed herein are methods for treating cancer, comprising administering to a subject in need thereof. IRX5183 and bortezomib.

Also disclosed herein are methods for treating cancer, comprising administering to a subject in need thereof an effective dose of a IRX5183 and bortezomib.

Also disclosed herein are methods for treating cancer, comprising administering to a subject in need thereof an effective dose of a IRX5183 and bortezomib, whereby as a result of the treatment the tumor burden is reduced in the subject.

BRIEF DESCRIPTION OF THE DRAWINGS

FIG. 1A-H depicts the relative concentration of plasma markers BCL6 (FIGS. 1A and E), BLIMP-1 (FIGS. 1B and F), XBPS-1 (FIGS. 1C and G), and CHOP (FIGS. 1D and H) and in multiple myeloma (MM) cell lines H929 (FIG. 1A-D) or CD138+MM cells from three different patient samples (FIG. 1E-H) incubated for 5 days either in the absence of stroma (Liquid), with or without AGN (RA receptor antagonist AGN194310, 1 µM), or cocultured with BM mesenchymal cells (Stroma), with or without R115 (CYP26 inhibitor R115866, 1 µM) or IRX (CYP26-resistant retinoid IRX5183, 1 µM). Expression in untreated liquid conditions was set at 1. Data are representative of 3 independent experiments with similar results and represent the mean±SEM. *P≤0.05 and **P≤0.01, by repeated-measures 1-way ANOVA for determination of statistical significance between groups; P values were corrected for multiple comparisons using Dunnett's test. Ctrl, control; max, maximum.

(FIG. 10A) CFU experiments with NB4 cells treated with $10^{-7}$ M ATRA, IRX5183, or $10^{-8}$ M AM80; (FIG. 10B) OCI-AML3 cells and (FIG. 10C) Kasumi-1 cells treated with $10^{-6}$ M ATRA, IRX5183, or $10^{-7}$ M AM80 showed a decrease in clonogenic growth compared to control with AM80 and IRX5183 both off and on stroma. Data across three independent experiments.

DETAILED DESCRIPTION

Figures 1E, 1F, 1G, 1H:
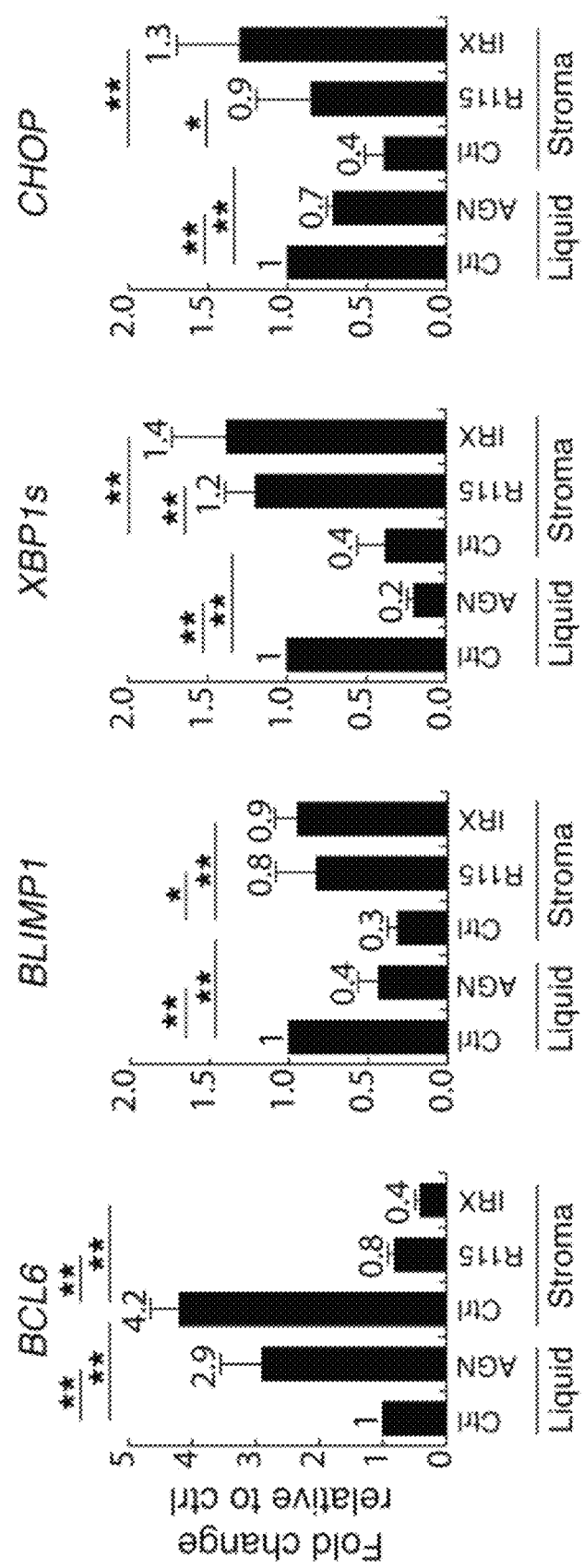

Disclosed herein are methods of treating cancer with CYP26-resistant, retinoic acid receptor (RAR) alpha (RARα) selective agonists and their use in the treatment of malignancies by acting upon cancer stem cells resident in the bone marrow.

Many, if not most, malignancies arise from a rare population of cells that exclusively maintain the ability to self-renew and sustain the tumor. These cancer stem cells are often biologically distinct from the bulk of differentiated cancer cells that characterize the disease. For example, chronic myeloid leukemia (CML) occurs at the level of hematopoietic stem cells and, like their normal counterparts, CML stem cells undergo orderly differentiation. Thus, the bulk of the leukemic mass in CML consists of differentiated blood cells, whereas the rare cells responsible for disease maintenance resemble normal hematopoietic stem cells. Similarly, in multiple myeloma, which is characterized by neoplastic plasma cells, these cells appear to be terminally differentiated like their normal counterparts. The myeloma plasma cells that form the bulk of the tumor arise from a population of less differentiated cancer stem cells that resemble post-germinal center B cells. Other cancers, including but not limited to, hematological malignancies, myelodysplastic syndrome, breast cancer, prostate cancer, pancreatic cancer, colon cancer, ovarian cancer, melanoma, non-melanoma skin cancers, and brain cancers have been demonstrated to arise from corresponding cancer stem cells.

Thus, disclosed herein are methods of treating cancer with agents which can target cancer stem cells in the protected bone marrow niche by inducing differentiation of the cancer stem cells into mature cancer cells that are susceptible to standard therapies. Administration of CYP26-resistant, RARα selective agonists which can act on the cancer stem cells in the bone marrow niche (because they are not inactivated by CYP26) is one such approach. In certain embodiments, effectiveness of therapy with a RARα selective agonist disclosed herein leads to a substantial decrease in the number of cancer stem cells in the bone marrow.

The cancer stem cells can be enumerated by various mechanisms and reduction in their numbers as a result of administration of a CYP26-resistant RARα selective agonist measured thereby. In embodiments disclosed herein, as a result of administration of a RARα selective agonist, the cancer stem cells in the bone marrow are reduced by more than about 0.5 log, more than about 1 log, more than about 1.5 log, more than about 2.0 log, more than about 2.5 log, more than about 3.0 log, more than about 3.5 log, more than about 4.0 log, more than about 4.5 log, or more than about 5.0 log.

Compounds with retinoid activity (vitamin A and its derivatives) have activity in cell proliferation and differentiation processes. Many biological effects of retinoids are mediated by modulating the nuclear retinoic acid receptors (RARs). The RARs activate transcription by binding to DNA sequence elements, known as RAR response elements (RARE), in the form of a heterodimer with one of the retinoid X receptors (known as RXRs). Three subtypes of human RARs have been identified and described: RARα, RARβ, and RARγ.

As used herein, the term "RARα agonist", is synonymous with "RARα selective agonist" and refers to a compound that selectively binds RARα. As used herein, the term "selectively binds," when made in reference to a RARα selective agonist, refers to the discriminatory binding of a RARα selective agonist to the indicated target RARα such that the RARα selective agonist does not substantially bind with non-target receptors like a RAR or a RARγ.

Selective binding of a RARα selective agonist to a RARα includes binding properties such as, e.g., binding affinity and binding specificity. Binding affinity refers to the length of time a RARα selective agonist resides at its a RARα binding site, and can be viewed as the strength with which a RARα selective agonist binds its a RARα. Binding specificity is the ability of a RARα selective agonist to discriminate between a RARα and a receptor that does not contain its binding site, such as, e.g., a RAR or a RARγ. One way to measure binding specificity is to compare the association rate of a RARα selective agonist for its RARα relative to the association rate of a RARα agonist for a receptor that does not contain its binding site; for example, comparing the association rate constant of a RARα selective agonist for its RARα relative to a RAR and/or a RARγ.

In some embodiments, a RARα selective agonist will have a ratio of activity at a RARα relative to a RAR and/or a RARγ of, e.g., at least 5 times greater, at least 10 times greater, at least 15 times greater, at least 20 times greater or at least 10,000 times greater. A RAR pan agonist will have activity at a RARα, a RARδ, and a RARγ, i.e., similar potency at a RARα, a RARδ, and a RARγ.

The binding specificity of a RARα selective agonist that selectively binds to a RARα can also be characterized as an activity ratio that such a RARα selective agonist can exert through binding to its RARα relative to a receptor not comprising its binding site, such as, e.g., a RAR or a RARγ. In some embodiments, a RARα selective agonist that selectively binds to a RARα has an activity ratio through its RARα relative to a receptor not comprising its binding site of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In some embodiments, a RARα selective agonist that selectively binds to a RARα has an activity ratio through its RARα relative to a RAR and/or a RARγ of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In some embodiments, a RARα selective agonist that selectively binds to a RARα has an activity ratio through its RARα relative to a receptor not comprising its binding site of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In some embodiments, a RARα selective agonist that selectively binds to a RARα has an activity ratio through its RARα relative to a RAR and/or a RARγ of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1.

RARα selective agonists useful in the methods disclosed herein are RARα selective agonists which are not metabolized by CYP26. CYP26 is a cytochrome P450 monooxygenase that metabolizes retinoic acid into inactive or less active substances which can also be readily eliminated from cells and regulates cellular levels of retinoic acid. RARα selective agonists that are readily metabolized by CYP26 are not within the scope of the present methods.

In an aspect of this embodiment, a CYP26-resistant RARα selective agonist is a compound having the structure of formula I,

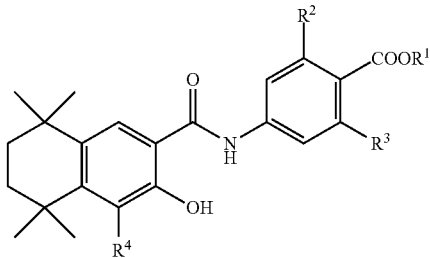

wherein $R^1$ is H or $C_{1-6}$ alkyl;
$R^2$ and $R^3$ are independently H or F; and
$R^4$ is a halogen.

In some embodiments of formula I, halogen is F, Cl, Br or I. In some embodiments, of formula I, halogen is F. In some embodiments, of formula I, halogen is Cl. In some embodiments, of formula I, halogen is Br. In some embodiments, of formula I, halogen is I.

In an aspect of this embodiment, a CYP26-resistant RARα selective agonist is a compound having a structure of formula II

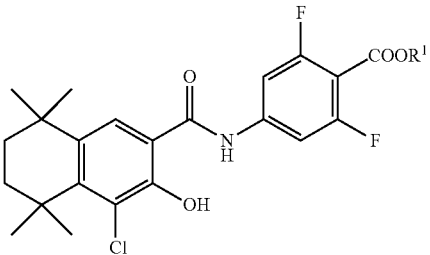

wherein $R^1$ is H or $C_{1-6}$ alkyl.

In another aspect of this embodiment, a CYP26-resistant RARα selective agonist is the compound having the structure of formula III

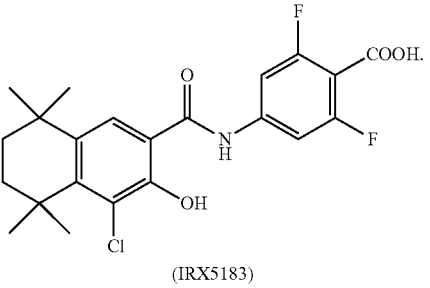

(IRX5183)

In another embodiment, a CYP26-resistant RARα selective agonist is tamibarotene (AM80; 4-[(5,6,7,8-tetrahydro-5,5,8,8-tetramethyl-2-naphthalenyl)carbamoyl]benzoic acid). In another embodiment, a CYP26-resistant RARα selective agonist is AM580 (4-[(5,6,7,8-tetrahydro-5,5,8,8-tetramethyl-2-naphthalenyl)carboxamido]benzoic acid). In another embodiment, a CYP26-resistant RARα selective agonist is Re 80 (4-[1-hydroxy-3-oxo-3-(5,6,7,8-tetrahydro-3-hydroxy-5,5,8,8-tetramethyl-2-naphthalenyl)-1-propenyl] benzoic acid).

As used herein, the term "CYP26-resistant" refers to RARα selective agonists which are not metabolized, degraded, or otherwise inactivated by the CYP26 enzyme and have activity within the bone marrow.

Assays by which a compound can be tested and established whether or not it is an RARα selective agonist are described in numerous prior art publications and patents. For example, a chimeric receptor transactivation assay which tests for agonist-like activity in the RARα, RARδ, RARγ, RXRα receptor subtypes, is described in detail in U.S. Pat. No. 5,455,265, which is hereby incorporated by reference for all it discloses regarding receptor transactivation assays.

The compounds and pharmaceutical compositions disclosed herein are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic tumors. The term "cancer" encompasses diseases of skin, tissues, organs, bone, cartilage, blood, and vessels. The term "cancer" further encompasses primary and metastatic cancers. Included within the term "cancer" are cancer stem cells.

In certain embodiments, the cancer is a hematologic malignancy. Non-limiting examples of hematologic malignancy include acute myeloid leukemia (AML), chronic myelogenous leukemia (CML), including accelerated CML and CML blast phase (CML-BP), acute lymphoblastic leukemia (ALL), chronic lymphocytic leukemia (CLL), Hodgkin's disease (HD), non-Hodgkin's lymphoma (NHL), including follicular lymphoma and mantle cell lymphoma, B-cell lymphoma, T-cell lymphoma, multiple myeloma (MM), Waldenstrom's macroglobulinemia, myelodysplastic syndromes (MDS), including refractory anemia (RA), refractory anemia with ringed sideroblasts (RARS), (refractory anemia with excess blasts (RAEB), and RAEB in transformation (RAEB-T), and myeloproliferative syndromes. In certain embodiments, when the cancer is a hematologic malignancy, the RARα selective agonist could be administered either as a stand-alone therapy in the absence of other anti-cancer treatments or in combination with other therapies, including but not limited to those listed below in Table 1.

In some embodiments, the cancer is a solid tumor. In other embodiments, the cancer is a solid tumor which can metastasize to the bone. Non-limiting examples of solid tumors that can be treated by the disclosed methods include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. In certain embodiments, when the cancer is a solid tumor, the RARα selective agonist is used in combination with a cytotoxic agent or other anti-cancer agent.

A compound disclosed herein, or a composition comprising such a compound, is generally administered to an individual as a pharmaceutical composition. Pharmaceutical compositions may be prepared by combining a therapeutically effective amount of at least one compound as disclosed herein, or a pharmaceutically acceptable acid addition salt thereof, as an active ingredient, with conventional acceptable pharmaceutical excipients, and by preparation of unit dosage forms suitable for therapeutic use. As used herein, the term "pharmaceutical composition" and refers to a therapeutically effective concentration of an active compound, such as, e.g., any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragée-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

Liquid dosage forms suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants. In liquid formulations, a therapeutically effective amount of a compound disclosed herein typically is between about 0.0001% (w/v) to about 50% (w/v), about 0.001% (w/v) to about 10.0% (w/v), or about 0.01% (w/v) to about 1.0% (w/v).

Solid dosage forms suitable for oral administration include capsules, tablets, pills, powders and granules. In such solid dosage forms, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); Remington: The Science and Practice of Pharmacy (Alfonso R. Gennaro ed., Lippincott, Williams & Wilkins, 20$^{th}$ ed. 2000); Goodman & Gilman's The Pharmacological Basis of Therapeutics (Joel G. Hardman et al., eds., McGraw-Hill Professional, 10$^{th}$ ed. 2001); and Handbook of Pharmaceutical Excipients (Raymond C. Rowe et al., APhA Publications, 4$^{th}$ edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the claimed methods.

"Administering", as used herein, refers to providing a pharmaceutical agent or composition to a subject, and includes, but is not limited to, administering by a medical professional and self-administering. Administration includes, but is not limited to, oral administration, nasal administration, pulmonary administration, subcutaneous administration, intravenous administration, intramuscular administration, intratumoral administration, intracavity administration, intravitreal administration, dermal administration, and transdermal administration, etc.

Depending on the type of cancer, and the patient to be treated, as well as the route of administration, the disclosed RARα selective agonists may be administered at varying therapeutically effective doses to a patient in need thereof.

However, the dose administered to a mammal, particularly a human, in the context of the present methods, should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

As a non-limiting example, when administering a RARα selective agonist disclosed herein to a mammal, a therapeutically effective amount generally may be in the range of about 1 mg/m$^2$/day to about 100 mg/m$^2$/day. In some embodiments, an effective amount of a RARα selective agonist disclosed herein may be about 5 mg/m$^2$/day to about 90 mg/m$^2$/day, about 10 mg/m$^2$/day to about 80 mg/m$^2$/day, about 15 mg/m$^2$/day to about 70 mg/m$^2$/day, about 20 mg/m$^2$/day to about 65 mg/m$^2$/day, about 25 mg/m$^2$/day to about 60 mg/m$^2$/day, or about 30 mg/m$^2$/day to about 55 mg/m$^2$/day. In some embodiments, a therapeutically effective amount of a compound or a composition disclosed herein may be at least 10 mg/m$^2$/day, at least 15 mg/m$^2$/day, at least 20 mg/m$^2$/day, at least 25 mg/m$^2$/day, at least 30 mg/m$^2$/day, at least 35 mg/m$^2$/day, at least 40 mg/m$^2$/day, at least 45 mg/m$^2$/day, at least 50 mg/m$^2$/day, at least 55 mg/m$^2$/day, at least 60 mg/m$^2$/day, at least 65 mg/m$^2$/day, or at least 75 mg/m$^2$/day. In some embodiments, a therapeutically effective amount of a RARα selective agonist disclosed herein may be at most 15 mg/m$^2$/day, at most 20 mg/m²/day, at most 25 mg/m²/day, at most 30 mg/m²/day, at most 35 mg/m²/day, at most 40 mg/m²/day, at most 45 mg/m²/day, at most 50 mg/m²/day, at most 55 mg/m²/day, at most 60 mg/m²/day, at most 65 mg/m²/day, at most 70 mg/m²/day, at most 80 mg/m²/day, at most 90 mg/m²/day, or at most 100 mg/m²/day.

Administration may be continuous or intermittent. The dosage may also be determined by the timing and frequency of administration. Thus, the RARα selective agonists disclosed herein can be given on a daily, weekly, or monthly basis for a period of time, followed by an optional drug holiday (drug free period) and that this drug administration/drug holiday cycle can be repeated as necessary.

In certain embodiments, the RARα selective agonist is administered in combination with one or more additional anti-cancer agents. Anti-cancer agents include cytotoxic drugs, including, but not limited to, paclitaxel, docetaxel, and the like and mixtures thereof. Additional anti-cancer agents include adriamycin, dactinomycin, bleomycin, vinblastine, cisplatin, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefmgol, chlorambucil, cirolemycin, cladribine, crisnatol mesylate, cyclophosphamide, cytarabine, dacarbazine, daunorubicin hydrochloride, decitabine, dexormaplatin, dezaguanine, dezaguanine mesylate, diaziquone, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2, interferon alfa-2a, interferon alfa-2b, interferon alfa-nI, interferon alfa-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride, and bortezomib.

In some embodiments, the anti-cancer agent includes, but is not limited to: 5-fluorouracil, 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, 9-dioxamycin, diphenyl spiromustine, docosanol, dolasetron, doxifluridine, droloxifene, dronabinol, duocarmycin SA, ebselen, ecomustine, edelfosine, edrecolomab, eflornithine, elemene, emitefur, epirubicin, episteride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leucovorin, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, oracin, oral cytokine inducer, ormaplatin, osaterone, oxaliplatin, oxaunomycin, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, pennyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone BI, ruboxyl, safmgol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen-binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer.

In some embodiments, the anti-cancer agent is one or more of an anthracycline (e.g., doxorubicin or epirubicin), cyclophosphamide, a platinum agent (e.g., cisplatin, carboplatin, oxaliplatin), a taxane (e.g., paclitaxel or docetaxel), methotrexate, 5-fluorouracil, trastuxumab, pertuzumab, vinorelbine, capecitabine, gemcitabine, mitoxantrone, ixabepilone, reibulin, an anti-hormone therapy (e.g., tamoxifen, anastrazole, exemestrane, letrozole), etoposide, irinotecan, vinblastine, pemetrexed, bevacizumab, cetuximab, an EGFR inhibitor (e.g., erlotinib), an EML4-ALK kinase inhibitor (e.g., crixotinil), estramustine, cytarabine, a demethylating agent (e.g., 5-azacytidine, decitabine), an immunomodulator (e.g., lenolidamide, pomalidomide), a corticosteroid, bleomycin, adriamycin, benamustin, fludarabine, a growth factor (GCSH, GM-CSF, EPO), and bortezomib.

Specific combinations of RARα selective agonists and additional anti-cancer agents useful in the treatment of cancer are listed below in Table 1. The listed drug combinations can be administered at the same time, at different times, in the same composition, in different compositions, in alternating times (1 week of RARα selective agonist followed by 1 week of another anti-cancer agent, etc.), or at any administration schedule established by a healthcare professional.

TABLE 1

| Cancer | Exemplary Drug combination |
|---|---|
| Breast | RARα selective agonist + an anthracycline (e.g., doxorubicin or epirubicin) + cyclophosphamide with or without a platinum agent (e.g., cisplatin or carboplatin) |
| | RARα selective agonist + an anthracycline + taxane (e.g., paclitaxel or docetaxel) with or without a platinum agent |
| | RARα selective agonist + cyclophosphamide + methotrexate + 5-fluorouracil with or without a platinum agent |
| | RARα selective agonist + an anthracycline + cyclophosphamide + 5-fluorouracil with or without a platinum agent |
| | RARα selective agonist + trastuzumab + a taxane |
| | RARα selective agonist + pertuzumab + trastuzumab + a platinum agent |
| | RARα selective agonist + vinorelbine with or without a platinum agent |
| | RARα selective agonist + capecitabine with or without a platinum agent |
| | RARα selective agonist + gemcitabine with or without a platinum agent |
| | RARα selective agonist + mitoxantrone with or without a platinum agent |
| | RARα selective agonist + ixabepilone with or without a platinum agent |
| | RARα selective agonist + eribulin with or without a platinum agent |
| | RARα selective agonist + an anthracycline with or without a platinum agent |
| | RARα selective agonist + a platinum agent |
| | RARα selective agonist + a taxane with or without a platinum agent |

TABLE 1-continued

| Cancer | Exemplary Drug combination |
|---|---|
| | RARα selective agonist + trastuzumab or pertuzumab with or without a platinum agent |
| | RARα selective agonist + cyclophosphamide with or without a platinum agent |
| | RARα selective agonist + methotrexate with or without a platinum agent |
| | RARα selective agonist + 5-fluorouracil with or without a platinum agent |
| | RARα selective agonist + a combination of two or more of a platinum agent, a taxane, gemcitabine, vinorelbine, capecitabine, cyclophosphamide, metotrexate, 5-fluorourocil, an anthracycline, trastuzumab, pertuzumab, mitoxantrone, ixabepilone, or eribulin. |
| | RARα selective agonist + trastuzumab |
| | RARα selective agonist + anti-hormone therapy (e.g., tamoxifen, anastrazole, exemestrane, letrozole) |
| Lung | RARα selective agonist + a platinum agent |
| | RARα selective agonist + etoposide |
| | RARα selective agonist + irinotecan |
| | RARα selective agonist + a platinum agent + etoposide |
| | RARα selective agonist + a platinum agent + irinotecan |
| | RARα selective agonist + a taxane |
| | RARα selective agonist + gemcitabine |
| | RARα selective agonist + vinorelbine |
| | RARα selective agonist + capecitabine |
| | RARα selective agonist + vinblastine |
| | RARα selective agonist + pemetrexed |
| | RARα selective agonist + bevacizumab |
| | RARα selective agonist + cetuximab |
| | RARα selective agonist + a combination of two or more of a platinum agent, etoposide, irinotecan, a taxane, gemcitabine, vinorelbine, capecitabine, vinblastine, pemetrexed, bevacizumab, or cetuximab |
| | RARα selective agonist + EGFR inhibitor (e.g.,erlotinib) |
| | RARα selective agonist + EML4- ALK kinase inhibitor (e.g., crizotinil) |
| Pancreas | RARα selective agonist + gemcitabine |
| | RARα selective agonist + erlotinib |
| | RARα selective agonist + 5-fluourouracil |
| | RARα selective agonist + irinotecan |
| | RARα selective agonist + a platinum compound |
| | RARα selective agonist + oxaliplatin |
| | RARα selective agonist + capecitabine |
| | RARα selective agonist + a taxane |
| | RARα selective agonist + a combination of two or more of a platinum agent, irinotecan, a taxane, gemcitabine, capecitabine, erlotinib, 5-fluorouracil, or oxaliplatin. |
| Prostate | RARα selective agonist + etoposide |
| | RARα selective agonist + a platinum agent |
| | RARα selective agonist + a taxane |
| | RARα selective agonist + vinorelbine |
| | RARα selective agonist + vinblastine |
| | RARα selective agonist + mitoxantrone |
| | RARα selective agonist + cabazitaxel |
| | RARα selective agonist + estramustine |
| | RARα selective agonist + an anthracycline |
| | RARα selective agonist + a combination of two or more of a platinum agent, etoposide, a taxane, vinorelbine, vinblastine, mitoxantrone, cabazitaxel, estramustine, or an anthracycline |
| Hematological Malignancies | RARα selective agonist + etoposide |
| | RARα selective agonist + an anthracycline (e.g., idarubicin, daunorubicin, mitoxantrone) |
| | RARα selective agonist + cytarabine |
| | RARα selective agonist + a combination of an anthracycline, cytarabine and etoposide |
| | RARα selective agonist + demethylating agent (5-azacytidine or decitabine) |
| | RARα selective agonist + small molecule inhibitors (e.g., thyrosine kinase inhibitors including BCR-ABL inhibitors, Flt3 inhibitors or cKit inhibitor, IDH1/2 inhibitors, JAK2 inhibitors, BTK inhibitors) |
| | RARα selective agonist + immunotherapeutic agents (monoclonal antibodies such as anti-CD33, anti-CD20, anti-CD19, anti-CD30or with PD1 inhibitors or CTL4 inhibitors) |
| | RARα selective agonist + immunomodulatory drugs such as lenolidamide, pomalidomide, and their derivatives |
| | RARα selective agonist + cyclophosphamide |
| | RARα selective agonist + bevacizumab |
| | RARα selective agonist + vincristine |
| | RARα selective agonist + a corticosteroid |
| | RARα selective agonist + bleomycin |
| | RARα selective agonist + adriamycin |
| | RARα selective agonist + bendamustin |
| | RARα selective agonist + fludarabine |
| | RARα selective agonist + growth factors including GCSF, GM-CSF and Epo |

TABLE 1-continued

| Cancer | Exemplary Drug combination |
|---|---|
| | RARα selective agonist + a combination of two or more of combinations listed above.<br>RARα selective agonist + bortezomib |

The effectiveness of cancer therapy is typically measured in terms of "response." The techniques to monitor responses can be similar to the tests used to diagnose cancer such as, but not limited to:

A lump or tumor involving some lymph nodes can be felt and measured externally by physical examination.

Some internal cancer tumors will show up on an x-ray or CT scan and can be measured with a ruler.

Blood tests, including those that measure organ function can be performed.

A tumor marker test can be done for certain cancers.

Regardless of the test used—whether blood test, cell count, or tumor marker test, it is repeated at specific intervals so that the results can be compared to earlier tests of the same type.

Response to cancer treatment is defined several ways:

Complete response—all of the cancer or tumor disappears; there is no evidence of disease. A tumor marker (if applicable) may fall within the normal range.

Partial response—the cancer has shrunk by a percentage but disease remains. A tumor marker (if applicable) may have fallen but evidence of disease remains.

Stable disease—the cancer has neither grown nor shrunk; the amount of disease has not changed. A tumor marker (if applicable) has not changed significantly.

Disease progression—the cancer has grown; there is more disease now than before treatment. A tumor marker test (if applicable) shows that a tumor marker has risen.

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products calculated. In the RECIST method, only the long axis is measured. If there are multiple solid tumors, the sum of all the long axes measurements is calculated. However, with lymph nodes, the short axis is measured instead of the long axis.

In some embodiments of the current method, the tumor burden of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In other embodiments, the 1-year survival rate of treated individual is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In other embodiments, the 5-year survival rate of treated individual is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In other embodiments, the 10-year survival rate of treated individual is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any other range bound by these values.

In yet other embodiments, the subject has a sustained remission of at least 6 months, at least 7 months, at least 8 months, at least 9 months, at least 10 months, at least 11 months, at least 12 months, at least 14 months, at least 16 months, at least 18 months, at least 20 months, at least 22 months, at least 24 months, at least 27 months, at least 30 months, at least 33 months, at least 36 months, at least 42 months, at least 48 months, at least 54 months, or at least 60 months or more.

As used herein, the term "substantially free of cancer" refers to a subject which does not have clinical evidence of cancer or cancer cells, or cancer stem cells.

In other embodiments, the method may help to treat or alleviate conditions, symptoms, or disorders related to cancer. In some embodiments, these conditions or symptoms may include, but are not limited to, anemia, asthenia, cachexia, Cushing's Syndrome, fatigue, gout, gum disease, hematuria, hypercalcemia, hypothyroidism, internal bleeding, hair loss, mesothelioma, nausea, night sweats, neutropenia, paraneoplastic syndromes, pleuritis, polymyalgia rheumatica, rhabdomyolysis, stress, swollen lymph nodes, thrombocytopenia, Vitamin D deficiency, or weight loss. In other embodiments, the administration of the RARα selective agonist prolongs the survival of the individual being treated.

EXAMPLES

Example 1. The Bone Marrow Niche Induces a Bortezomib Resistance in Multiple Myeloma Multiple myeloma (MM) is characterized by the proliferation of malignant plasma cells (PCs) within the BM and their production of monoclonal immunoglobulin (Ig). Novel therapies, including proteasome inhibitors, have significantly extended the survival of patients with MM but have failed to achieve a cure. Increasing evidence demonstrates that interactions with the BM microenvironment play a critical role in the survival of MM cells during chemotherapy. However, the mechanisms mediating this BM niche-dependent chemoprotection are incompletely understood and remain a critical area of research.

There exist MM cells that resemble mature B cells and are resistant to bortezomib (BTZ). Like their normal B cell counterparts, these CD138− MM cells are capable of clonogenic growth and differentiation into CD138+ PCs. Moreover, these cells are enriched during minimal residual disease (MRD), suggesting a critical role in disease relapse. Differential BTZ sensitivity of CD138+ and CD138−MM cells may be explained by their secretory activity. As a result of their abundant Ig production, CD138+ PCs are highly dependent on an intact proteasome pathway to degrade improperly folded proteins. Conditions that disrupt protein degradation by the proteasome activate a cellular stress pathway known as the unfolded protein response (UPR), which counteracts ER stress by decreasing protein synthesis and promoting protein degradation. If homeostasis cannot be reestablished, UPR activation eventually leads to apoptosis. On the other hand, CD138−MM cells exhibit limited Ig production and low ER stress and are less dependent on proteasome-mediated degradation of misfolded proteins.

Methods

Cell cultures. All cell lines were purchased from the American Type Culture Collection. H929, MM1s, and U266 cells were cultured in RPMI 1640 with 10% FCS (Sigma-Aldrich), 2 mM L-glutamine, and 100 µg/ml penicillin-streptomycin (P/S). OP-9 cells were cultured in α-MEM, 20% FCS, L-glutamine, and P/S. Cell lines were authenticated by short-tandem repeat profiling.

Primary MM cells were obtained from patients with newly diagnosed or relapsed MM under an IRB-approved protocol at The Johns Hopkins University. Briefly, mononuclear cells were isolated from fresh BM aspirates by density gradient centrifugation (Ficoll-Paque); CD138+ cells were then selected via magnetic beads and columns and incubated in RPMI 1640, 10% FCS, L-glutamine, and P/S at 37° C.

Primary human BM stromal cells were derived from aspirates collected from healthy donors under an IRB-approved protocol at Johns Hopkins. Briefly, total mononuclear cells isolated from BM aspirates were cultured in Iscove's modified Dulbecco's medium (IMDM) supplemented with 10% horse serum, 10% FCS, 10-5 M hydrocortisone 21-hemisuccinate, P/S, and 0.1 mM β-mercaptoethanol (p-ME) (FBMD1 media). The following day, cells in suspension were removed by washing twice with PBS, and the media were replaced. Attached stromal cells were incubated at 33° C. until a confluent monolayer was obtained. Mouse primary BM stromal cells were isolated following the same protocol, after isolation of total BM mononuclear cells from mouse femurs.

Vectors and viral supernatants. To generate Smo-KO and WT stroma, BM stromal cells were derived from $Smo^{fl/fl}$ mice and transduced with the retroviral vector PIG-Cre encoding Cre-recombinase (Addgene; catalog 50935) or a control vector (Addgene; catalog 18751), respectively. Successfully infected cells were selected using 4 µg/ml puromycin for 5 days and confirmed by expression of GFP via flow cytometry. The pLenti-CMV-LUC-Puro lentiviral vector (plasmid 17477) was used to generate H929 Luc+ cells.

To generate CYP26A1-overexpressing stromal cells, WT and Smo-KO stromal cells were transduced with the lentiviral vector pBABE-neo (Addgene; catalog 1767) that had been engineered to encode CYP26A1. Briefly, Cyp26a1 cDNA (Origene) was amplified via PCR using primers incorporating the restriction sites BamHI and EcoRI and cloned into the pCR2.1 vector. Cyp26a1 cDNA was confirmed via Sanger sequencing, and the fragment was isolated after digestion with the restriction enzymes BamHI and EcoRI and subcloned into the corresponding sites of the pBABE vector. Lentiviral particles were produced as previously described. Successfully infected stromal cells were selected using 3 µg/ml G-418 for 10 days, and expression of Cyp26a1 was confirmed by qRT-PCR.

Coculture experiments. 24-well plates were coated with 0.1% gelatin in PBS for 30 min at 37° C. The gelatin solution was removed, and the stromal cells were cultured overnight at a density of $5 \times 10^4$ cells/well to obtain a confluent monolayer. At that time, MM cell lines or primary MM cells ($1 \times 10^5$ in 2 ml) were added to the stroma cultures. The stroma cocultures were incubated at 37° C. in RPMI containing 10% FCS, L-glutamine, and P/S, with or without AGN19194310 (1 µM for 5 days), R115866 (1 µM for 5 days), IRX5183 (1 µM for 5 days), or BTZ (2.5 nM for 48 hr).

Transwell experiments. For Transwell experiments, 6-well plates were coated with 0.1% gelatin in PBS for 30 min at 37° C. The gelatin solution was removed, and the stromal cells were cultured overnight in FBMD1 media at a density of $10 \times 10^4$ cells/well in 2 ml of media to obtain a confluent monolayer. At that time, Transwell inserts (Corning) were placed over the stroma cultures, and MM cell lines ($1 \times 10^6$ in 1 ml) were seeded in the Transwell for 24 hr at 37° C. Following this incubation, Transwell and MM cells were removed, and stromal cells were detached from the wells and analyzed by qRT-PCR for CYP26 expression.

Mobilization experiments. MM cells were separated from BM stromal cells by gently pipetting several times around the well. Detached cells were centrifuged, resuspended in fresh media, and incubated in a 24-well plate for 1 hr at 37° C. During this short incubation period, contaminating stromal cells attached to the well, while MM cells remained in suspension. MM cells were then recovered by gently pipetting. This protocol was used for qRT-PCR and CFU coculture experiments. The purity achieved using this protocol was confirmed by flow cytometry to be 98%-99% MM cells and less than 2% contaminating stroma.

Clonogenic assays. After treatment, MM cells were collected, washed with PBS, and plated at a density of 5,000 cells/ml in 1 ml of 1.32% methylcellulose supplemented with 30% FBS, 10% BSA, L-glutamine, P/S, and 0.1 mM p-ME. Cells were plated in triplicate in 35-mm culture dishes, incubated at 37° C., and scored for the presence of colonies 14 days later.

qRT-PCR. Total RNA was extracted using the RNeasy Mini Kit (QIAGEN) according to the manufacturer's instructions. cDNA was synthesized by reverse transcription using the iScript cDNA Synthesis Kit (Bio-Rad). qRT-PCR was performed with iTaq SYBR Green Supermix (Bio-Rad) using sequence specific primers. Gene expression was normalized to GAPDH, and relative quantification was calculated using ΔΔCt. All experiments were performed in duplicate and run on the Bio-Rad CFX96 machine.

Flow cytometry. Following treatment, MM cells were collected, washed with PBS, and stained for 15 min at room temperature with phycoerythrin-conjugated (PE-conjugated) anti-CD138. Cells were washed to remove unbound antibody and evaluated in a FACSCalibur system (BD Biosciences). Stromal cells were identified by GFP expression, and viable cells were identified using 7-aminoactinomycin D (7-AAD). To calculate cell numbers, live GFP-cells were normalized to calibration beads.

Mouse xenografts. $1 \times 10^6$ H929 Luc+ cells and $1 \times 10^6$ mouse BM stromal cells were resuspended in 100 µl Matrigel, diluted with RPMI (1:1), and injected subcutaneously into 16-week-old male NSG mice. After 4 days, treatment with BTZ (0.5 mg/kg i.p. twice weekly) and IRX (10 mg/kg i.p. daily) was initiated. Tumor burden was assessed by bioluminescence using the In Vivo Imaging System (PerkinElmer). For imaging, mice were exposed to 120 mg/kg D-luciferin via intraperitoneal injection 10-5 min before imaging and were anesthetized using isoflurane. Images were analyzed with Living Image Software, version 2.5 (PerkinElmer), and data were quantified as photons/second.

For the systemic MM model, $2 \times 10^6$ Luc+/GFP+H929 cells were injected via the tail vein into 16-week-old male NSG mice. After engraftment, as determined by an exponential increase in bioluminescence, mice were treated with BTZ (0.5 mg/kg i.p.) twice weekly and with IRX (10 mg/kg) once daily. Tumor burden was assessed by bioluminescence, as above.

Statistics. First evaluated was whether the treatment groups were different from the controls using 1-way ANOVA. If the ANOVA test yielded a statistically significant result, then the difference between the control group and each treatment group was evaluated, with the P values adjusted for multiple comparisons using Dunnett's test. For experiments in which only 2 sets of data were analyzed, statistical significance was evaluated using an unpaired, 2-tailed Student's t test. Pearson's R value for correlation and P values were calculated using GraphPad Prism 7 (GraphPad Software).

Results

The BM niche limits PC differentiation by modulating retinoid signaling. A population of MM progenitors, phenotypically similar to B cells, is intrinsically resistant to BTZ and contributes to MRD and relapse. To investigate whether the BM niche plays a role in determining the phenotype of MM cells, the mRNA expression of B cell and PC markers in MM H929 cell lines (FIG. 1A-D) and MM CD138+ primary cells (FIG. 1E-H) was analyzed following coculture with mouse BM stroma using human-specific primers. B cell lymphoma 6 (BCL6), a transcriptional repressor that promotes self-renewal of germinal center B cells and prevents PC differentiation, was upregulated in the presence of BM stromal cells (FIG. 1A, 1E). In contrast, coculture of MM cells with BM stroma decreased the mRNA expression of B lymphocyte-induced maturation protein 1 (BLIMP1) and spliced X box-binding protein 1 (XBP1s) (FIG. 1B, C, F, G), which are critical mediators of PC differentiation. Similarly, C/EBP homologous protein (CHOP), a key component of the UPR pathway, was downregulated in the presence of BM stromal cells (FIG. 1D, H).

The BM niche regulates hematopoietic stem cell (HSC) differentiation by expressing the retinoid-inactivating enzyme CYP26. CYP26 enzymes were highly expressed in BM mesenchymal cells, while their expression was barely detectable in MM cells. Since retinoid signaling promotes PC differentiation and potentiates Ig secretion, it was determined whether stromal CYP26 is responsible for inducing a B cell phenotype in MM cells. To this end, coculture conditions were treated with the CYP26 inhibitor R115866 (R115) or the CYP26-resistant RA receptor α-selective (RARα-selective) retinoid IRX5183 (IRX). Incubation of stroma cocultures with either R115 or IRX restored all markers to levels comparable to those of liquid control conditions (FIG. 1A-H). Moreover, treatment of MM cells with the pan-RAR antagonist AGN194310 (AGN) mimicked the changes induced by BM stromal cells (FIG. 1A-H), limiting PC differentiation.

Expression of CD138 is a hallmark of normal PC differentiation as well MM PCs. Consistent with mRNA levels of PC markers, surface CD138 expression was markedly decreased by coculture with BM stromal cells or incubation with AGN. Incubation of BM stromal cell cocultures with R115 or IRX restored CD138 expression in MM cells. R115 did not significantly affect the expression of differentiation markers in liquid conditions by quantitative reverse transcription-PCR (qRT-PCR) or flow cytometry, while IRX induced comparable changes, irrespective of the presence or absence of BM stroma. Taken together, these data suggest that retinoid signaling promotes PC differentiation of MM cells and that this process is blocked by stromal CYP26-mediated metabolism of RA.

Figure 2A:
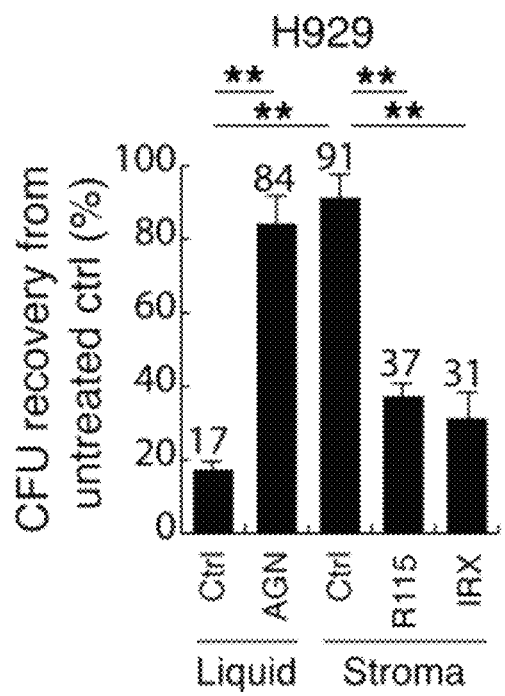
FIG. 2A-B depicts the clonogenic recovery (CFU) of H929 cells (FIG. 2A) or cellular recovery of primary CD138+MM cells from 3 different patient samples (FIG. 2B). MM cells were treated with BTZ (2.5 nM) for 48 hours after being incubated for 5 days either in the absence of stroma (Liquid), with or without the pan-RAR inhibitor AGN (1 μM), or in the presence of BM mesenchymal cells (Stroma), with or without the CYP26 inhibitor R115 (1 μM) or the CYP26-resistant retinoid IRX (1 μM). Clonogenic or cellular recovery was normalized to each condition in the absence of BTZ.
Figure 2B:
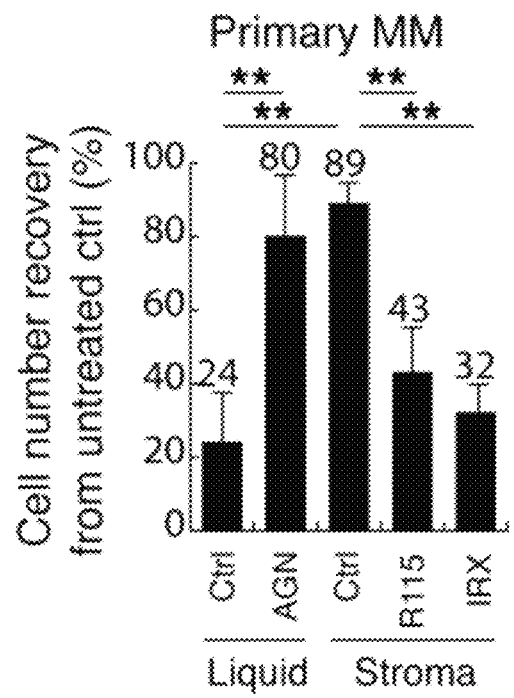

A RA-low microenvironment induces BTZ resistance. To determine whether decreased retinoid signaling contributes to BTZ resistance within the BM niche, MM cell lines and MM CD138+ primary cells were incubated with BM stroma for 5 days, followed by BTZ treatment. In the absence of BM stroma (liquid), MM cells were highly sensitive to BTZ (FIG. 2A-B). However, incubation with BM stroma induced BTZ resistance, which was overcome by CYP26 inhibition via R115 or by the CYP26-resistant retinoid IRX. Moreover, treatment of MM cells with the pan-RAR antagonist AGN mimicked the changes induced by BM stromal cells (FIG. 3), decreasing BTZ sensitivity.

Figure 3:
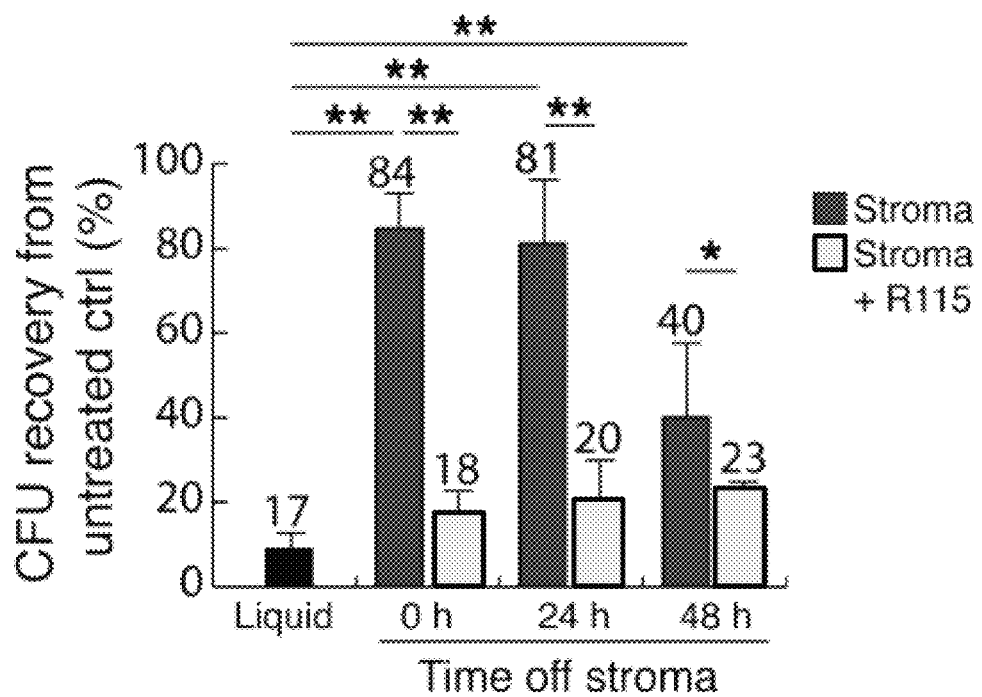
FIG. 3 depicts clonogenic recovery of H929 cells treated with BTZ (2.5 nM). MM cells were incubated for 5 days in the absence (Liquid) or presence of BM mesenchymal cells (Stroma), with or without R115 (1 μM). Following this preincubation, H929 cells were separated from BM stroma, cultured in fresh media for 0 to 48 hours, and then treated with BTZ (2.5 nM) for 48 hours. Clonogenic recovery was normalized to each condition in the absence of BTZ.

Strategies to overcome microenvironment-dependent chemoprotection have focused on mobilization of cancer cells from the BM niche into the peripheral circulation. It was analyzed whether the change in phenotype and subsequent BTZ resistance of MM cells were lost upon separation from the BM stroma, a process that mimics mobilization. To this end, H929 cells were separated from BM mesenchymal cells following a 5-day stroma coculture, incubated in fresh media (RPMI with 10% FBS) for 0 to 48 hr, and then treated with BTZ. Interestingly, MM cells remained partially resistant to BTZ for up to 48 hr following detachment from stroma (FIG. 3). Moreover, treatment of the coculture conditions with R115 prevented the development of a BTZ-resistant phenotype (FIG. 3). Thus, microenvironment-dependent BTZ resistance induced by the change in MM cell phenotype may not immediately be reversed by tumor mobilization.

Figure 4:
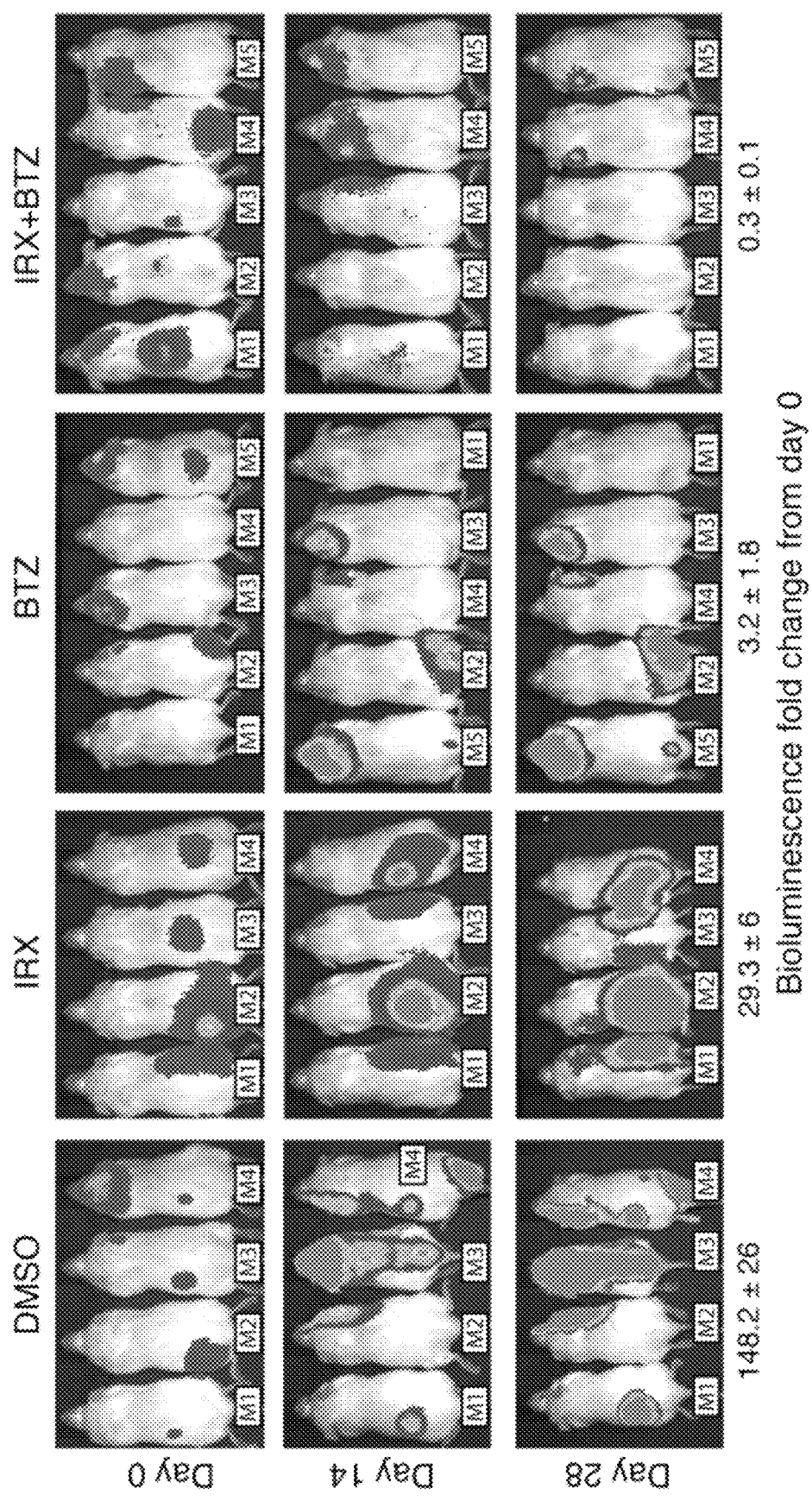
FIG. 4 depicts bioluminescent images of systemic MM xenografts. Following engraftment of H929 Luc+ cells, mice were treated with IRX (n=4), BTZ (n=5), or a combination of both (n=5) for 4 weeks. Data represent the mean±SEM of the fold change in bioluminescence (photons/second) from day 0.

To test whether retinoids can enhance BTZ activity in MM, a systemic MM xenograft was developed by injecting $2 \times 10^6$ H929 luciferase+(Luc+) cells via the tail vein of nonobese, diabetic, severe combined immunodeficiency IL-2 receptor γ-KO (NSG) mice. The animals were randomized to receive IRX, BTZ, or a combination of both, and disease burden was followed weekly by bioluminescence imaging (FIG. 4). Mice treated with BTZ showed decreased tumor growth compared with untreated controls; however, some MM cells remained resistant to BTZ, as demonstrated by the continued increase in bioluminescence. Similarly, mice treated with IRX monotherapy showed a decrease in tumor burden compared with untreated mice. Most important, IRX sensitized MM cells to BTZ, leading to a significant ($P<0.01$) decrease in disease burden. Collectively, these data suggest that an RA-low microenvironment created by stromal CYP26 induces a BTZ-resistant phenotype, which is maintained even after displacement from the BM niche.

Figures 5A, 5B, 5C:
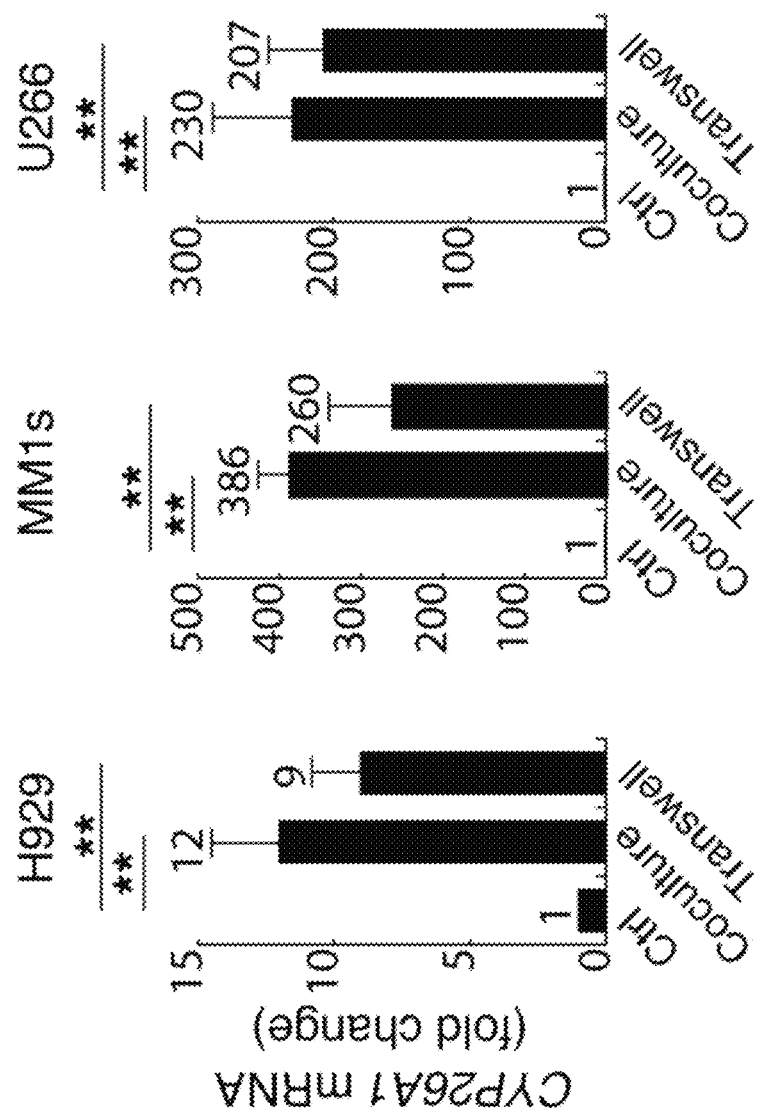
FIG. 5A-C depicts the effects of MM cells on the expression of CYP26A1 in BM stroma. Relative quantification of CYP26A1 mRNA in human BM mesenchymal cells incubated for 24 hours either in the absence (Ctrl) or presence (Coculture or Transwell) of MM cells (H929 [FIG. 5A], MM1s [FIG. 5B], U266 [FIG. 5C]). Expression in untreated BM stroma (Ctrl) was arbitrarily set at 1.

MM cells induce stromal CYP26. Recent studies have demonstrated the existence of a bi-directional crosstalk, in which not only stromal cells provide a protective microenvironment, but also cancer cells actively adapt and build a reinforced niche. Thus, it was determined whether MM cells reinforce a protective microenvironment by strengthening the ability of BM stroma to inactivate retinoids. Stromal CYP26 expression was analyzed by qRT-PCR in BM mesenchymal cells following a 24-hr coculture with MM cells. The isoenzyme CYP26A1 was highly upregulated by all 3 MM cell lines tested (FIG. 5A-C). In contrast, the isoenzyme CYP26B1 showed little to no changes in mRNA levels. Conditioned media derived from MM cells also upregulated CYP26A1 in BM stromal cells, although to a lesser extent. This could be explained by the presence of physical interactions in coculture experiments, or the lack of continuous production of soluble ligands by MM cells in conditioned media experiments. Consistent with the latter, stromal CYP26A1 was highly upregulated when MM and BM stromal cells were separated by a Transwell that prevented physical contact but allowed the diffusion of soluble factors (FIG. 5A-C).

MM cells produce a variety of soluble factors including cytokines (IL-1, IL-3, IL-6, TNF-$\alpha$) as well as Hedgehog ligands such as sonic hedgehog (SHH), which could impact the BM stromal compartment. Therefore, it was determined whether any of these factors was responsible for the observed upregulation of CYP26A1 on BM stromal cells. Of the soluble factors tested, only SHH produced a sustained overexpression of CYP26A1, while IL-1, IL-3, IL-6, and TNF-$\alpha$ had no significant effects. Whereas SHH is expressed by BM stromal cells and thus may be able to activate the Hedgehog pathway in an autocrine manner, its expression was considerably higher in MM cells compared with that detected in BM stroma, suggesting that paracrine activation may play a dominant role. Consistent with this, there was a statistically significant correlation between the mRNA levels of SHH in MM cells and activation of stromal Hedgehog signaling as determined by protein patched homolog 1 (PTCH1) expression. Moreover, activation of stromal Hedgehog significantly correlated with CYP26A1 upregulation. Specifically, MM1S cells with the highest expression of SHH also induced the highest expression of both PTCH1 and CY26A1 in stromal cells. SHH has a half-life of less than 1 hr, which may explain the reduced effect of MM-conditioned media on stromal CYP26A1 expression compared with that observed in coculture and Transwell experiments.

Figure 6A:
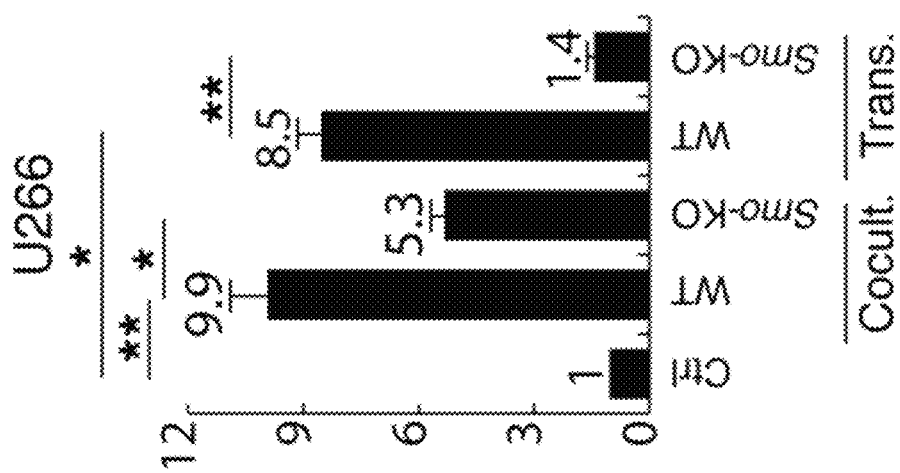
FIG. 6A-C depicts the relative quantification of CYP26A1 mRNA in mouse wild type (WT) or Smo-KO BM stroma incubated for 24 hr in the absence (Ctrl) or presence (Coculture or Transwell) of MM cells (H292, MM1s, U266). Expression in untreated WT or Smo-KO stroma was arbitrarily set at 1 for the respective treated conditions. Data represent the mean±SEM of 3 independent experiments. *$P \leq 0.05$ and **$P \leq 0.01$, by unpaired, 2-tailed Student's t test.
Figure 6B:
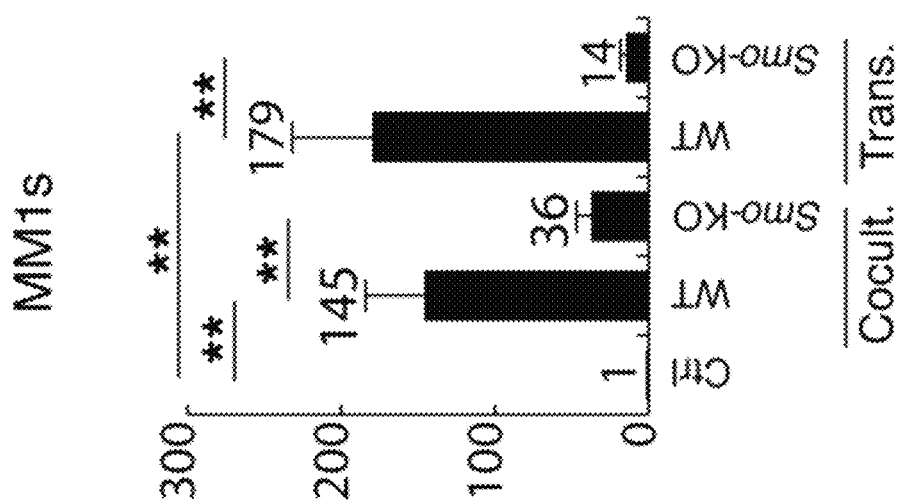
Figure 6C:
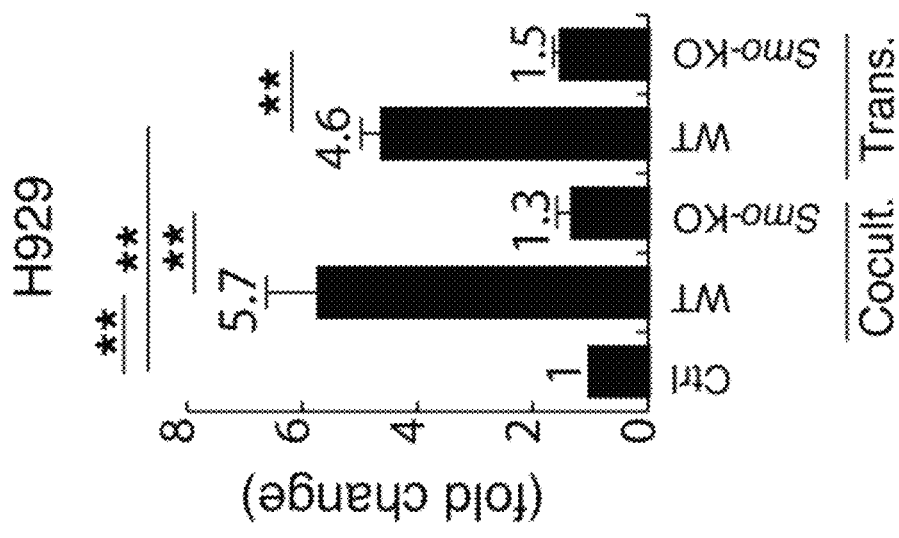

To confirm the role of paracrine Hedgehog on this interaction, smoothened (Smo), a membrane receptor that transduces SHH signaling, was knocked out at the genomic level in the mesenchymal compartment. For this, BM mesenchymal cells derived from Smo$^{fl/fl}$ mice were transduced with a retroviral vector encoding Cre recombinase (Smo-KO stroma). Mouse Smo$^{fl/fl}$ stromal cells transduced with an empty retroviral vector were used as a control (WT stroma). The transduced BM stromal cells were cocultured with MM cells for 24 hr. As expected, Smo-KO stroma had a decreased ability to upregulate Cyp26a1 in response to MM cells compared with WT stroma (FIG. 6A-C). Similarly, the SMO inhibitor cyclopamine partially overcame stromal Cyp26a1 upregulation by MM cells. These data suggest that MM cells modulate stromal CYP26 expression at least in part via paracrine SHH.

Paracrine Hedgehog produced by MM cells reinforces a protective microenvironment. Given the observations that stromal CYP26 activity may be responsible for BTZ resistance in MM cells, it was assessed whether paracrine Hedgehog secreted by MM cells reinforces a chemoprotective niche by regulating retinoid metabolism. It was first investigated whether modulation of Hedgehog signaling paralleled the retinoid-dependent phenotypes observed previously. Disruption of paracrine Hedgehog signaling in Smo-KO stroma cocultures partially restored PC differentiation (downregulation of BCL6 and upregulation of BLIMP1, XBP1, and CHOP) in H929 (FIG. 9A-D) and primary CD138+MM cells (FIG. 9E-H). Surface expression of CD138 was also restored in the presence of Smo-KO stroma. As expected, these findings were associated with an increased sensitivity to BTZ of MM cells treated in the presence of Smo-KO stroma compared with WT stroma.

To demonstrate that paracrine Hedgehog indeed induces a BTZ-resistant phenotype by increasing the ability of BM stroma to inactivate retinoids, Cyp26a1 expression in Smo-KO stroma was rescued via lentivirus-mediated gene transfer (pBABE-Cyp26a1) in order to achieve comparable CYP26A1 levels in WT (WT-Cyp26a1) and Smo-KO (Smo-KO-Cyp26a1) stromal cells. If the role of paracrine Hedgehog was independent of retinoid signaling, the relative inability of Smo-KO stroma to induce a B cell phenotype and BTZ resistance should have persisted even after Cyp26a1 upregulation. However, Cyp26a1 overexpression rescued the ability of Smo-KO stroma to induce a B cell phenotype and restored the expression of differentiation markers and BTZ resistance to levels comparable to those detected in WT and WT-Cyp26a1 stroma coculture conditions. This finding is consistent with the hypothesis that paracrine Hedgehog reinforces a protective niche via Cyp26a1 upregulation.

Figure 7:
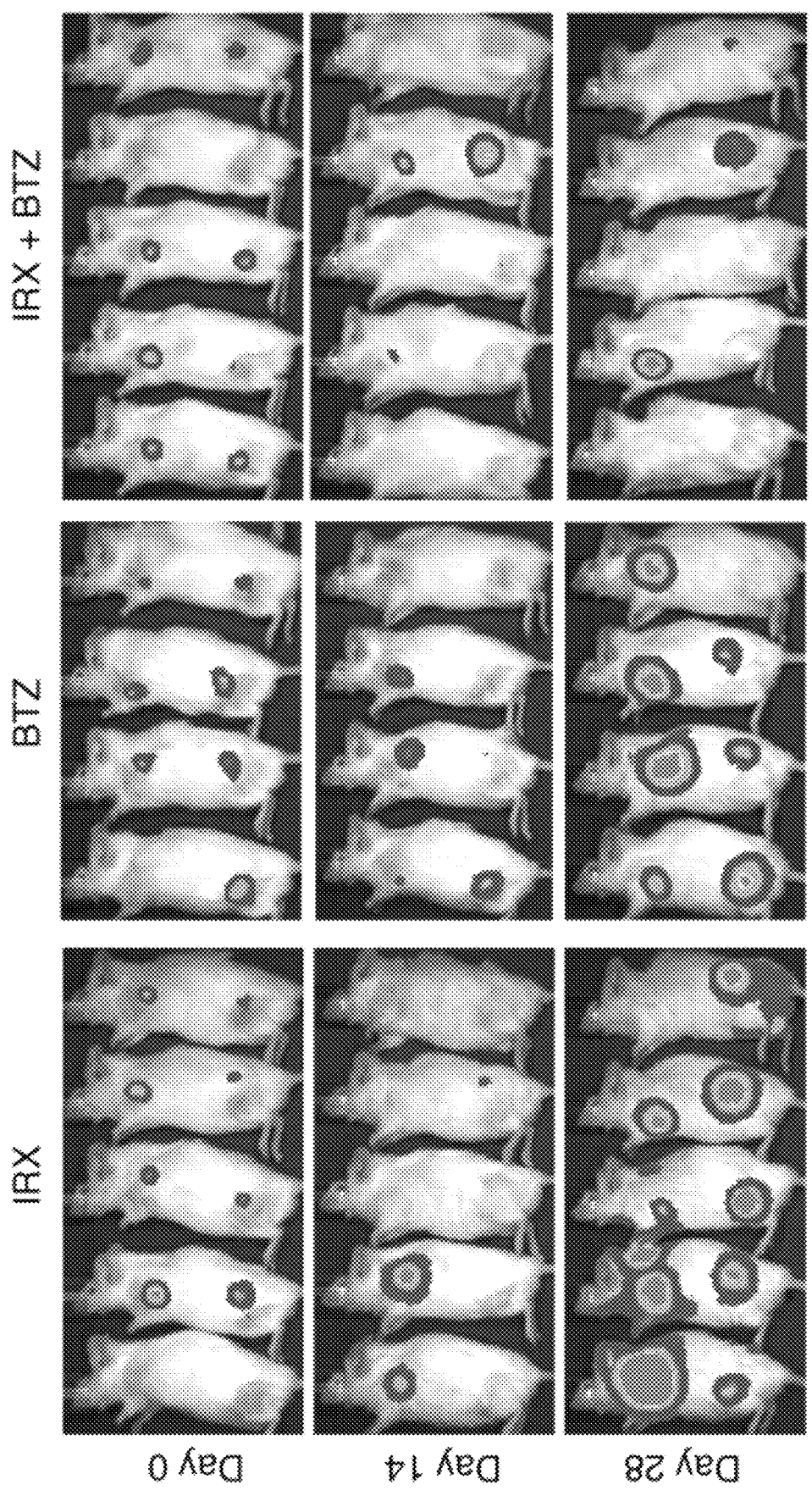
FIG. 7 depicts bioluminescent images of mice showing tumor burden during 4 weeks of treatment with IRX (10 mg/kg), BTZ (0.5 mg/kg), or the combination. Anterior tumors consisted of a combination of MM1S luciferase+ cells and $Smo^{Fl/Fl}$ BM stroma cells transduced with a control vector (WT BM stroma). Posterior tumors consisted of a combination of MM1S luciferase+ cells and $Smo^{Fl/Fl}$ BM stroma cells transduced with Cre-recombinase (Smo KO BM stroma).
Figure 8:
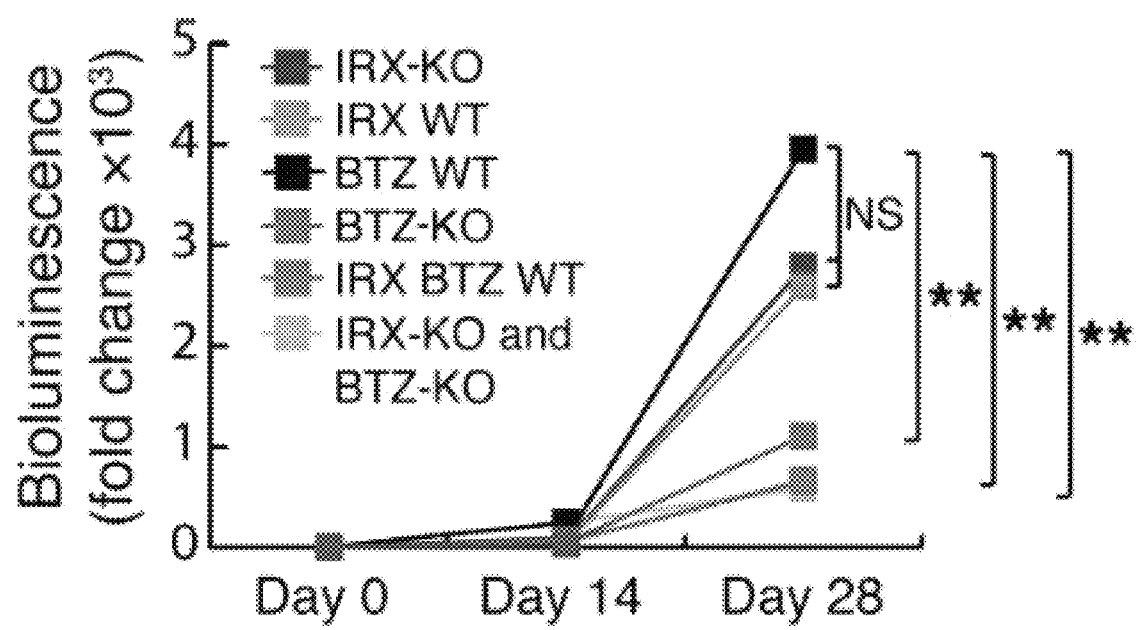
FIG. 8 depicts the fold change in bioluminescence (photons/second) of tumors during 4 weeks of treatment. The change in bioluminescence for each tumor at day 1 was normalized to the change in bioluminescence at day 14 and at the end of treatment (day 28).
Figures 9A, 9B, 9C, 9D:
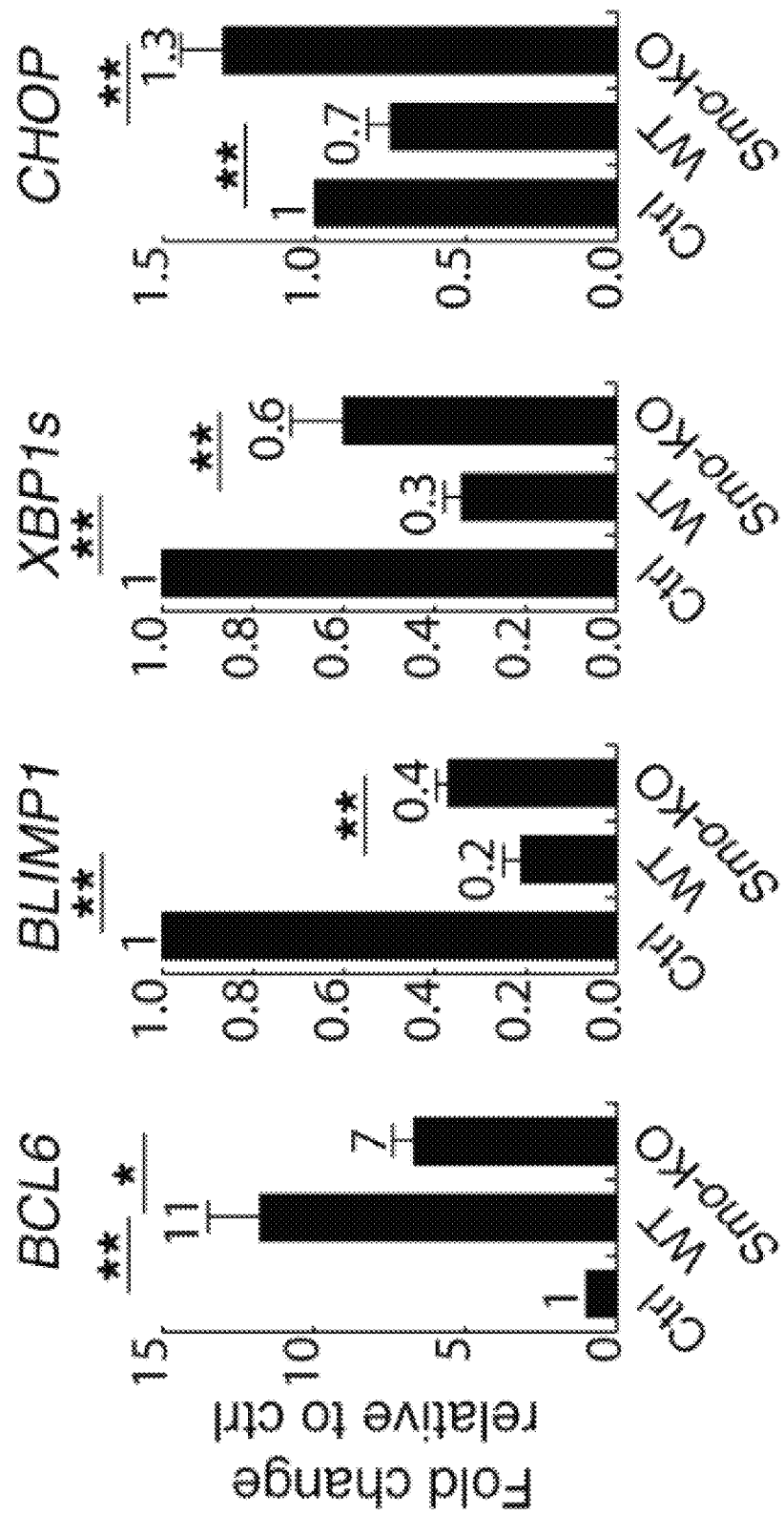
FIG. 9A-H depicts the relative quantification of BCL6 (B cell marker), BLIMP, XBP1s, and CHOP (PC markers) in H929 cells (FIG. 9A) and primary CD138+MM cells (FIG. 9B) from 3 different patient samples incubated for 5 days either in the absence of stroma (Ctrl) or cocultured with WT or Smo-KO stromal cells. Expression in untreated liquid conditions was set at 1. Data represent the mean±SEM. *$P \leq 0.05$ and **$P \leq 0.01$, by repeated-measures 1-way ANOVA to determine statistical significance between treatment groups; P values were corrected for multiple comparisons using Dunnett's test.
Figures 9E, 9F, 9G, 9H:
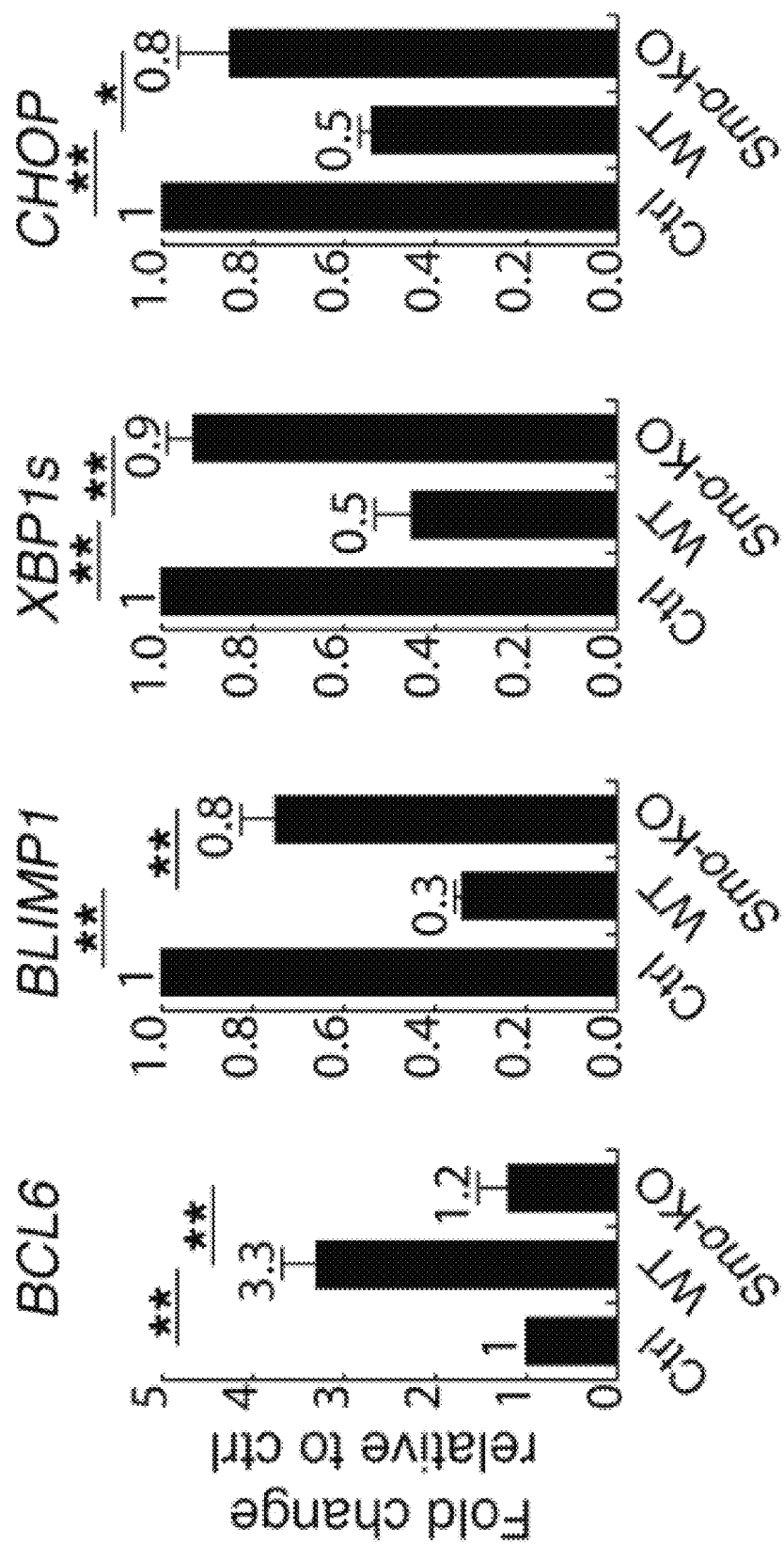

To study to what extent an RA-low environment created by the BM stroma and enhanced by MM cells via paracrine Hedgehog signaling contributes to BTZ resistance, a xenograft model of MM-niche interactions was developed. Each mouse carried 2 subcutaneous tumors consisting of H929 Luc+ cells and either WT (anterior tumors) or Smo-KO stroma (posterior tumors). Mice were treated with IRX (10 mg/kg i.p. daily), BTZ (0.5 mg/kg i.p. twice weekly), or a combination of both. The growth of tumors bearing WT or Smo-KO stroma was not different in untreated or IRX-treated groups (FIGS. 7 and 8). Consistent with in vitro data, tumors with WT stroma were refractory to BTZ treatment, as determined by an exponential increase in bioluminescence, while tumors carrying Smo-KO stroma showed a significant response (FIG. 8). Moreover, the combination of IRX and BTZ resulted in a significant and equivalent response, regardless of the phenotype of the stromal compartment (FIG. 8). While some tumors in the treatment group receiving combined IRX and BTZ appeared to have regressed completely, even after anatomical study, this was not the case for all the mice in this group. Flow cytometric analyses of the tumors after treatment revealed no differences in the in vivo growth of WT or Smo-KO stroma. Taken together, these data suggest that paracrine Hedgehog secreted by MM cells modulates retinoid signaling and BTZ sensitivity in the BM niche via CYP26A1 upregulation.

Given their high secretion of Ig, PCs are particularly sensitive to proteasome inhibition, and this accounts for the high remission rates achieved in MM patients treated with this family of drugs. Nonetheless, BTZ has failed to achieve a cure. A population of MM cells, phenotypically similar to B cells, survive BTZ treatment and are able to differentiate into PCs and recapitulate the original disease. Despite efficient elimination of MM PCs, these MM B cells survive BTZ treatment and become the predominant cell population during MRD. Consequently, new therapeutic strategies targeting MM B cells are required. A retinoid-low microenvironment created by stromal CYP26 maintained an immature, BTZ-resistant phenotype in MM. Thus, these data reveal a therapeutic opportunity to overcome BTZ resistance in the MM microenvironment using CYP26-resistant retinoids.

Despite being extensively studied in many hematological malignancies, the use of retinoids as differentiation therapy has proved beneficial only in patients with acute promyelocytic leukemia (APL). CYP26 expression by BM stromal cells may explain the lack of a clinical benefit of natural retinoids, despite their in vitro activity. Recent studies have highlighted the efficacy of CYP-resistant synthetic retinoids in differentiating cancer cells and sensitizing them to targeted therapy. For instance, AM80 differentiates FMS-like tyrosine kinase 3/internal tandem duplication (FLT3/ITD) acute myeloid leukemia (AML) cells and increase their sensitivity to FLT3 inhibitors. Similarly, synthetic retinoids reverse a stem cell phenotype in BCR-ABL1+ leukemic lymphoblasts and substantially increase their responsiveness to tyrosine kinase inhibitor (TKI) therapy in vivo. Such strategies to bypass stromal CYP26 could expand the clinical effectiveness of retinoid therapy.

MM cells utilize physical contacts to maintain drug resistance and survive within the BM niche. Thus, therapeutic strategies to overcome stromal chemoprotection have focused on mobilization of malignant cells from the BM niche by targeting adhesion molecules or chemokines such as CXCR4. MM cells exposed to a retinoid-low microenvironment acquire a BTZ-resistant phenotype that is maintained even after these cells are displaced from their niche. Initial clinical studies have shown improved response rates in relapse/refractory patients receiving the CXCR4 inhibitor plerixafor in combination with BTZ; however, this data suggest that such mobilization approaches may be insufficient to eliminate MM B cells.

Recent studies have demonstrated the existence of a bidirectional communication, in which not only stromal cells provide a chemoprotective niche, but also cancer cells actively shape and reinforce their microenvironment. The role of paracrine Hedgehog has been studied extensively in solid malignancies. In this system, ligands secreted by cancer cells activate the Hedgehog pathway in neighboring stromal cells, enhancing their chemoprotective properties via incompletely understood mechanisms. This data suggest that paracrine Hedgehog may work at least in part by increasing the ability of stroma to inactivate retinoids through upregulation of CYP26 and thus to maintain a BTZ-resistant phenotype in MM. Interestingly, CYP26 upregulation is associated with an "activated stromal subtype" and a significantly worse prognosis in patients with pancreatic cancer, a disease in which paracrine Hedgehog signaling is well established. The extent to which Hedgehog ligands produced by cancer cells contribute to this "activated" stromal phenotype and high CYP26 levels is unknown. Moreover, BM mesenchymal cells migrate and become a relevant cell population in the stromal compartment of these tumors.

The endosteal region is the primary niche of MM, AML, and micrometastatic disease from solid tumors. Within the osteoblastic region, these cancer cells maintain a quiescent, stem cell phenotype and are protected from chemotherapy-induced apoptosis. It is likely that these cancer cells rely on the same cues from the BM microenvironment as normal hematopoietic stem cells do to survive chemotherapy and perpetuate the disease. The BM microenvironment protected MM and AML cells by directly inactivating various chemotherapy agents via expression of CYP3A4 and other detoxifying enzymes. Another potential mechanism of microenvironment-mediated drug resistance is now demonstrated: creation of a retinoid-low niche that maintains a drug-resistant B cell phenotype. A CYP26-resistant retinoid potentiated the activity of BTZ against MM in the BM niche provides a therapeutic opportunity to bypass this mechanism of resistance.

Example 2. CYP26-Resistant RARα Agonists Overcome Bone Marrow (BM) Protection of AML by CYP26

Figure 10A:
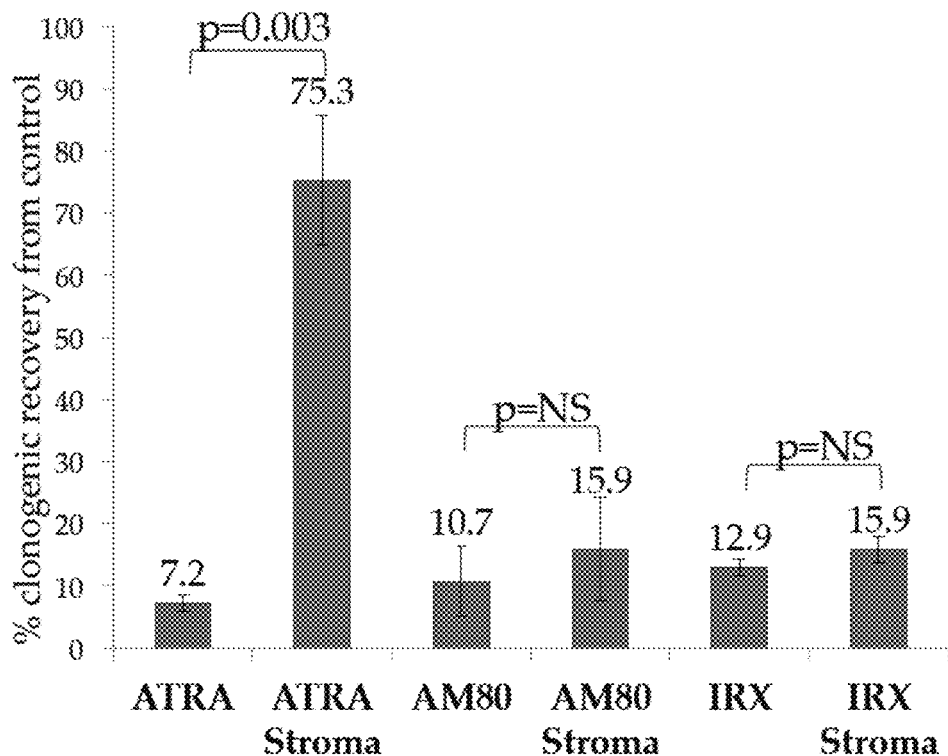
FIG. 10A-C depicts stroma blockage of ATRA-mediated, but not AM80- or IRX5183-induced, differentiation and elimination of AML.
Figure 10B:
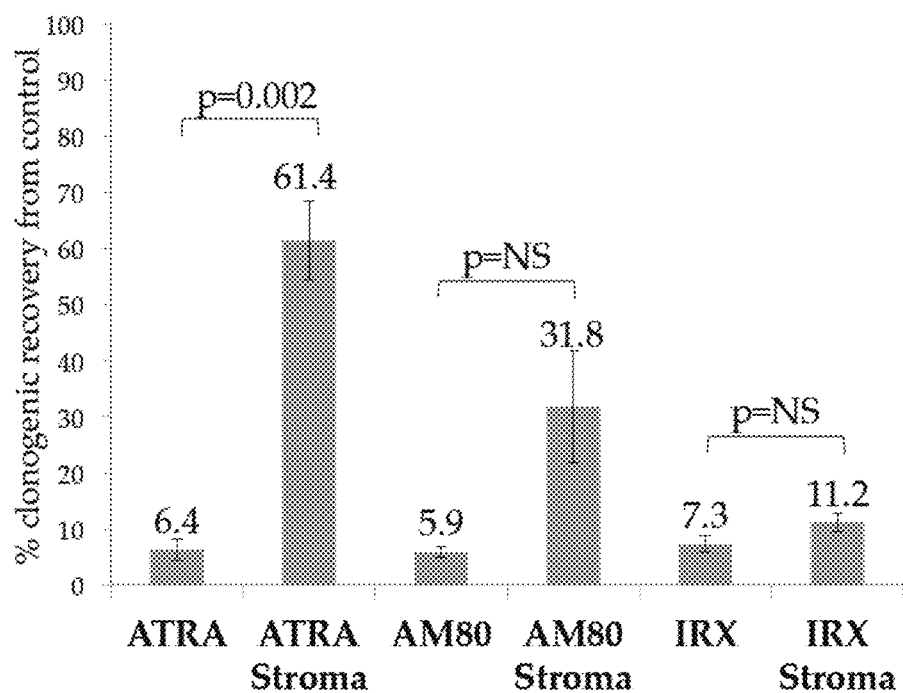
Figure 10C:
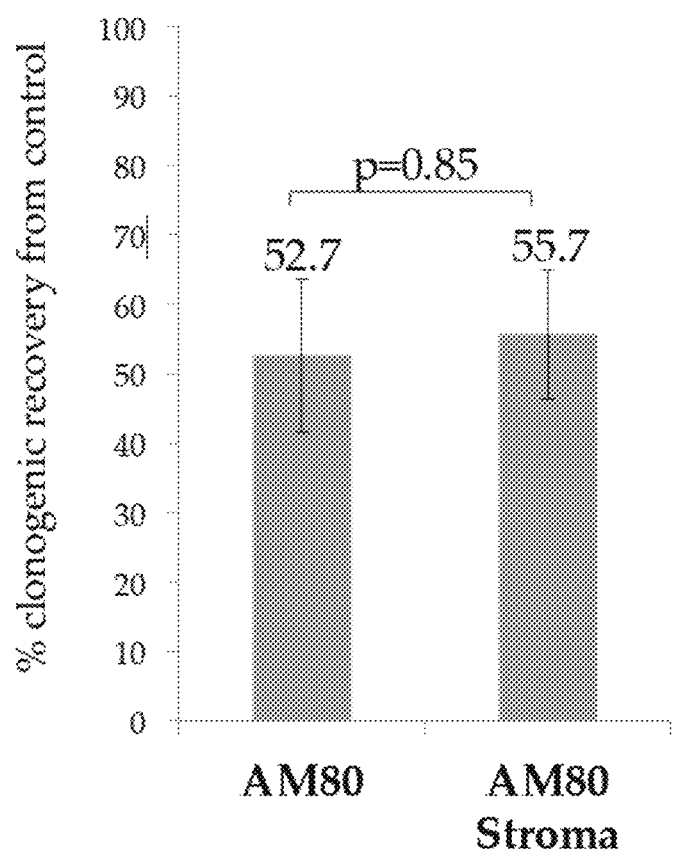

All-trans retinoic acid (ATRA), acting through RARα, causes terminal differentiation and apoptosis of non-APL AML cells in vitro but is clinically ineffective against AML. The BM stroma, which expresses inducibly high levels of CYP26, metabolically inactivates ATRA and provides a protected environment for AML cancer stem cells. Synthetic, CYP26-resistant RARα agonists, such as IRX5183 and AM80, should be able to bypass stroma-mediated protection of AML cells and differentiate the cancer stem cells resident in the protected environment of bone marrow niche. To test these hypotheses, clonogenic growth experiments were conducted in the non-APL AML cell lines OCI-AML 3 and Kasumi-1 and APL NB4 cells, which were treated with ATRA, IRX5183, and AM80 in the presence or absence of stroma. ATRA inhibited clonogenic growth only in the absence of stroma. In contrast, IRX5183 inhibited clonogenic growth to a similar extent in the presence or absence of stroma (FIG. 10A-C). AM80 also inhibited clonogenic growth in the presence of stroma but not as effectively as IRX5183. These data indicate that CYP26-resistant, RARα agonists such as IRX5183 may be effective treatments for AML by overcoming stromal mechanisms of drug resistance.

Example 3. Phase I/II Clinical Study of IRX5183 in Relapsed and Refractory Myeloid Malignancies Acute myeloid leukemia (AML) is successfully treated in only 30-40% of younger patients and very few older patients with standard chemotherapy regimens. Given the clinical activity of all-trans retinoic acid (ATRA; retinoic acid, RA) in acute promyelocytic leukemia (APL), ATRA was considered an attractive therapeutic strategy for other AML subtypes. APL, and most non-APL AMLs undergo terminal differentiation and are therefore successfully treated by ATRA in vitro. However, ATRA has not proven effective in non-APL AMLs in clinical trials.

Retinoic acid (RA) plays a significant role in the differentiation of hematopoietic stem cells (HSCs). The cytochrome P450 enzyme CYP26, expressed in bone marrow (BM) stromal cells, inactivates RA, thereby limiting differentiation of HSCs. Several AML cell lines, both APL and non-APL, are sensitive to RA-induced differentiation, but this effect was abrogated in the presence of BM stroma. Thus, it may be useful to treat AML with a retinoid that is resistant to metabolism by the CYP26 pathway. IRX5183 is a RARα selective agonist which is resistant to CYP26 metabolism. Use of IRX5183 in AML provides a novel targeted approach to this disease, which has the potential to change the prognosis of this and other hematologic malignancies. Thus, a phase I/II clinical trial will be conducted of IRX5183 in relapsed/refractory AML and high risk myelodysplastic syndrome (HR-MDS).

Study Objectives

Dose Escalation Phase Primary Objectives:

1) Evaluate safety and toxicity associated with administration of IRX5183 in patients with relapsed and refractory AML by determining the dose limiting toxicities (DLT) and maximally-tolerated dose (MTD).

2) Determine pharmacokinetic (PK) parameters of IRX5183 in the peripheral blood.

Dose Escalation Phase Secondary Objectives:

1) Determine the PK parameters of IRX5183 in the bone marrow.

2) Define differentiation profiles associated with IRX5183, BM cellular retinoid concentrations, blast counts, and cytogenetics at different dose levels.

Dose Expansion Phase Primary Objectives:
1) Define differentiation markers, BM retinoid concentrations, blast counts, and cytogenetics in AML and HR-MDS patients at the optimal dose level.
2) Obtain preliminary efficacy data of IRX5183 in terms of complete response (CR), partial response (PR), and hematological improvement (HI) in both cohorts of patients.

Dose Expansion Phase Secondary Objectives:
1) Define toxicity profiles of IRX5183 at the optimal dose in both patient cohorts.
2) Obtain data on correlations between IRX5183-induced differentiation and toxicity and clinical responses.

Eligibility criteria—dose escalation/determination. This phase will only recruit patients with AML:
1. Patients must be able to understand and voluntarily sign an informed consent form.
2. Age 18-70 years at the time of signing the informed consent.
3. Able to adhere to the study visit schedule and other protocol requirements.
4. Life expectancy of greater than 6 months.
5. Must have pathologically confirmed AML with one or two prior courses of induction chemotherapy or hypomethylating agent therapy or relapsed after complete remission, before or after allogeneic bone marrow transplant, AND no plans for further intensive chemotherapy.
6. Patients must not have received any other treatment for their disease (aside from hydroxyurea for control of blast count in AML patients), including hematopoietic growth factors, within three weeks of beginning the trial, and should have recovered from all toxicities of prior therapy (to grade 0 or 1).
7. ECOG performance status of 2 at study entry, or Karnofsky 60%.
8. Laboratory test results within these ranges:
   a. Calculated creatinine clearance by MDRD (CrCL) >50 ml/min/1.73 squared meter
   b. Total bilirubin 2.0 mg/dL unless due to Gilbert's syndrome, hemolysis, or ineffective hematopoiesis AST (SGOT) and ALT (SGPT) ≤3×ULN
9. Females of childbearing potential must have negative pregnancy test.
10. Patients must have no clinical evidence of CNS or pulmonary leukostasis, disseminated intravascular coagulation, or CNS leukemia.
11. Patients must have no serious or uncontrolled medical conditions.

Eligibility criteria—dose expansion. This phase will recruit patients with relapsed/refractory AML (cohort 1) and patients with HR-MDS not responding to hypomethylating agents (cohort 2) and will follow the noted eligibility criteria above (aside from #5 above in MDS patients), including pathologically confirmed CMML or MDS with high risk features at the time of referral as defined by:
1. INT-2 or high IPSS score
2. Secondary MDS
3. INT-1 MDS with excess blasts 5% blasts in BM) or RBC or platelet transfusion-dependency
4. CMML with 5% marrow blasts, or RBC or platelet transfusion-dependency, abnormal karyotype, or proliferative features All HR-MDS patients are required to have failed or relapsed after an initial response to hypomethylating agents or have refused to receive hypomethylating therapy. Failure to respond is defined as failing to achieve a CR, PR or HI after at least 4 cycles of hypomethylating therapy.

Treatment Plan

For the dose escalating phase, IRX5183 is administered orally in daily doses continually in 28 day cycles until toxicity or disease progression. Bone marrow testing during each of the first 4 cycles determines marrow status and response. Only patients with relapsed or refractory AML are enrolled in the dose escalation phase. The starting dose (DL1) of single agent IRX5183 is 30 mg/m$^2$/day, and the individual dosing levels are noted below:

| Dose level (DL) | Daily dose (mg/m$^2$) |
| --- | --- |
| DL(−1) | 15 |
| DL1 | 30 |
| DL2 | 45 |
| DL3 | 60 |
| DL4 | 75 |

The phase-expansion part of the study uses the optimal dose identified in the phase-escalation part of the study and includes two separate arms; one for AML patients and another for HR-MDS, and each of these two arms will recruit 26 patients.

Dose levels are explored according to a traditional 3+3 design, with an aim to enroll 3 subjects at a time to determine the toxicity profile of IRX5183 in AML patients. If none of the three patients receiving DL1 experiences a DLT, another three patients will be treated at the next higher dose level. However, if one of the first three patients experiences a DLT, three more patients will be treated at the same dose level. The dose escalation will continue until at least two patients among a cohort of 3-6 patients experience DLTs. If two or more patients experience DLT on DL1, the next patient will be recruited to DL(−1). The MTD of single agent IRX5183 will be the highest dose at which 0 or 1 DLT are seen in a cohort of six subjects.

For the phase 2 dose expansion cohort, patients with AML are continued to be enrolled at the MTD, with goal of enrolling 26 patients (inclusive of patients treated at the MTD in first phase of the trial). Patients continue on single agent IRX5183 until they experience toxicity or disease progression. If patients achieve a complete remission, they have the option to consolidate with transplant, chemotherapy, and/or continue on maintenance IRX5183. If patients achieve a partial response or hematologic improvement they have the option to obtain salvage therapy in combination with IRX5183. For MDS patients, the phase 2 dose expansion cohort will recruit 26 patients who receive single agent IRX5183 at the MTD from the first phase of the trial. They also continue until undue toxicity or disease progression. Patients who achieve hematologic improvement or better have the option to consolidate with transplant, combine with demethylating agent therapy, or continue on maintenance IRX5183.

Pharmacokinetics Analyses

Plasma concentrations of IRX5183 are evaluated for the escalation and expansion phases, targeting safe and effective retinoid levels by pharmacokinetics using LCM-MS (liquid chromatography-mass spectroscopy tandem). Targeting peak levels of 1 µM should avoid systemic toxicity, while presumably preserving local BM niche retinoid levels. The plasma concentration of IRX5183 are obtained using a single 2 mL blood sample, pre-dose on day 14. Samples are shipped to and analyzed by the designated analytical laboratory.

Pharmacodynamics Analyses

In addition to assessing standard clinical response criteria, BM cellular (normal HSCs and LSCs) concentrations, peripheral blood and bone marrow blast counts, markers of differentiation, apoptosis, and clonogenic growth are determined. A bone marrow aspirate and biopsy are obtained at baseline, on day 14, and at the end each of the first 4 cycles of therapy. Differentiation is assessed using flow cytometry, comparing expression of differentiation markers on CD45 positive cells and ALDHint LSCs on day 14 marrow versus baseline. FISH analysis is also conducted after each cycle for patients with baseline abnormalities to determine if leukemic clone still present on day 14.

Expected outcomes: Patients receiving RARα selective agonist are monitored for response criteria based on hematological parameters including complete blood counts and percentage of leukemia blasts in the peripheral blood and in the bone marrow. Patients with improved neutrophil count, decreased transfusion requirements of red blood cells and platelets together with decreased percentage of blasts in the bone marrow and induction of differentiation and apoptosis of these malignant blasts are deemed responsive to therapy. Quality of life parameters such as pain, performance status and participation in activity of daily living and instrumental activities of daily living are assessed to evaluate the impact of this therapy on study patients. Use of this RARα selective agonist is expected to improve hematological and quality of life parameters in patients with MDS/AML and solid malignancies. In addition, the use of the RARα agonist which is CYP26 resistant may result in differentiation and thus elimination of minimal residual disease in the bone marrow of these patients.

The ultimate goal is to develop better treatments for patients with relapsed/refractory AML and this study will provide valuable insights into the use of novel retinoids in this setting.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for treating acute myeloid leukemia other than acute promyelocytic leukemia (non-APL AML) consisting of administering to a subject in need thereof an effective dose of a CYP26-resistant retinoic acid receptor alpha (RARα) selective agonist and a Flt3 inhibitor, wherein the CYP26-resistant RARα selective agonist is

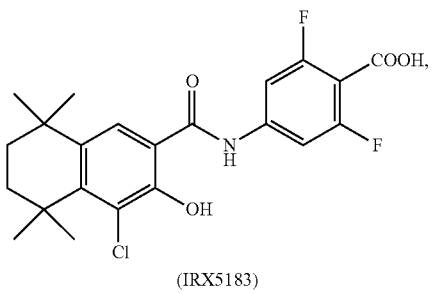

(IRX5183)

and optionally, at least one additional anti-cancer agent selected from the list consisting of etoposide, an anthracycline, idarubicin, daunorubicin, mitoxantrone, cytarabine, a combination of an anthracycline, cytarabine and etoposide, a demethylating agent, 5-azacytidine, decitabine, a proteasome inhibitor, bortezomib, a tyrosine kinase inhibitor, a BCR-ABL inhibitor, a Flt3 inhibitor, a cKit inhibitor, an IDH1/2 inhibitor, a JAK2 inhibitor, a BTK inhibitor, an immunotherapeutic monoclonal antibody (mAb), anti-CD33 mAb, anti-CD20 mAb, anti-CD19 mAb, anti-CD30 mAb, anti-PD1 mAb, anti-CTLA4 mAb, lenalidomide, pomalidomide, cyclophosphamide, bevacizumab, vincristine, a corticosteroid, bleomycin, adriamycin, bendamustin, fludarabine, G-CSF, GM-CSF, Epo, and combinations thereof;

whereby as a result of the treatment the tumor burden, including tumor burden in the bone marrow niche, is reduced in the subject.

2. The method according to claim 1, consisting of administration of the effective dose of the CYP26-resistant RARα selective agonist, Flt3 inhibitor, and the at least one additional anti-cancer agent.

3. The method according to claim 2, wherein the at least one additional anti-cancer agent comprises an immunotherapeutic mAb.

4. The method according to claim 3, wherein the immunotherapeutic mAb is an anti-CD33 mAb.

5. The method according to claim 3, wherein the immunotherapeutic mAb is an anti-CD20 mAb.

6. The method according to claim 3, wherein the immunotherapeutic mAb is an anti-CD30 mAb.

7. The method according to claim 3, wherein the immunotherapeutic mAb is an anti-PD1 mAb.

8. The method according to claim 2, wherein the at least one additional anti-cancer agent comprises a proteasome inhibitor.

9. The method according to claim 8, wherein the proteasome inhibitor is bortezomib.

10. The method according to claim 1, wherein the at least one additional anti-cancer agent comprises a proteasome inhibitor.

11. The method according to claim 10, wherein the proteasome inhibitor is bortezomib.

* * * * *